(12) United States Patent
McKee et al.

(10) Patent No.: US 10,077,285 B2
(45) Date of Patent: Sep. 18, 2018

(54) ENHANCED FUNCTIONALITY AND DELIVERY OF A PROTEIN FROM A POROUS SUBSTRATE

(71) Applicant: Bio-Rad Laboratories, Inc., Hercules, CA (US)

(72) Inventors: Clayton T. McKee, Davis, CA (US); William Strong, El Cerrito, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 0 days.

(21) Appl. No.: 15/667,478

(22) Filed: Aug. 2, 2017

(65) Prior Publication Data

US 2018/0009840 A1    Jan. 11, 2018

Related U.S. Application Data

(62) Division of application No. 14/340,364, filed on Jul. 24, 2014, now Pat. No. 9,738,683.

(60) Provisional application No. 61/858,488, filed on Jul. 25, 2013.

(51) Int. Cl.
*C07K 1/22* (2006.01)
*C07K 1/113* (2006.01)

(52) U.S. Cl.
CPC .............. *C07K 1/1136* (2013.01); *C07K 1/22* (2013.01)

(58) Field of Classification Search
None
See application file for complete search history.

(56) References Cited

U.S. PATENT DOCUMENTS

| | | |
|---|---|---|
| 4,632,901 A | 12/1986 | Valkirs et al. |
| 5,183,809 A | 2/1993 | Weisz et al. |
| 5,957,593 A | 9/1999 | Kroon |
| 8,206,664 B2 | 6/2012 | Lin |
| 9,594,054 B2 | 3/2017 | McKee et al. |
| 9,671,402 B2 | 6/2017 | McKee |
| 2006/0160078 A1 | 7/2006 | Cardy et al. |
| 2006/0189533 A1 | 8/2006 | Quay et al. |
| 2007/0117173 A1* | 5/2007 | Levison .................. C12N 9/96 435/23 |
| 2010/0184687 A1 | 7/2010 | Staby et al. |
| 2010/0239459 A1 | 9/2010 | Alajem et al. |
| 2011/0165081 A1 | 7/2011 | Schulke et al. |
| 2013/0131323 A1 | 5/2013 | Van Alstine et al. |
| 2013/0164193 A1 | 6/2013 | Semenov et al. |
| 2014/0029284 A1 | 1/2014 | McKee et al. |

FOREIGN PATENT DOCUMENTS

| | | |
|---|---|---|
| WO | 1999/52934 A | 10/1999 |
| WO | 2003/020924 A2 | 3/2003 |
| WO | 2005/116081 A2 | 12/2003 |
| WO | 2013/109825 A1 | 7/2013 |

OTHER PUBLICATIONS

International Search Report and Written Opinion dated Oct. 15, 2014 for International Patent Application No. PCT/US2014/048072, 10 pages.
International Search Report and Written Opinion dated Jun. 3, 2015 for International Patent Application No. PCT/US2015/018165, 10 pages.
Extended European Search Report dated Feb. 23, 2017 in EP 14830330.8, 8 pages.
Carrilho et al., "Understanding Wax Printing: A Simple Micropatterning Process for Paper-Based Microfluidics," Anal. Chem., vol. 81, No. 16, pp. 7091-7095 (2009).
Chothia et al., "Canonical Structures for the Hypervariable Regions of Immunoglobulins", *J. Mol. Biol.*, 196, 901-917 (1987).
Chothia et al., "Structural Repertoire of the Human VH Segments", *J. Mol. Biol.*, vol. 227, pp. 799-817 (1992).
GE Healthcare. "Principles of ion exchange", *Ion Exchange Chromatography and Chromatofocusing.*, pp. 1-185. http://www.gelifesciences.com/gehcis_images/GELS/Related%20Content/Files/1314623637792/litdoc11000421_20140926235100.pdf.
Goyal et al., "LEA proteins prevent protein aggregation due to water stress", *Biochem J.*, vol. 388 (pt. 1), pp. 151-157 (2005).
Hamada, Hiroyuki, et al: "Effect of Additives on Protein Aggregation", Current Pharmaceutical Biotechnology, Jun. 1, 2009, vol. 10, No. 4, pp. 400-407.
Jallerat & Thom, Filter Membranes and Bioseparation Equipment and Supplies, IVD Technology (Oct. 2004).
Kolb et al., "Click Chemistry: Diverse Chemical Function from a Few Good Reactions", *Agnew Chem.* vol. 40, pp. 2004-2021 (2001).
Kurganov, B. I., "Antiaggregation activity of chaperones and its quantification", Biochemistry, Jan. 12, 2014, vol. 78, No. 13, pp. 1554-1566.
Lefranc, "IMGT, the international ImMunoGeneTics database", *Nucleic Acids Res.*, vol. 29, No. 1, pp. 207-209 (2001).
Lu et al., "Rapid prototyping of paper-based microfluidics with wax for low-cost, portable bioassay," *Electrophoresis*, vol. 30, 1497-1500 (2009).
Martin et al, "Modeling antibody hypervariable loops: A combined algorithm", *Proc. Natl. Acad. Sci. USA*, vol. 86, pp. 9268-9272 (1989).
Moores et al., "Sequence Dependence of Protein Isoprenylation", The *Journal of Biological Chemistry*, vol. 266, No. 22, pp. 14603-14810 (1991).
Otzen, D.E. et al.; Structural basis for cyclodextrins suppression of human growth hormone aggregation; *Protein Science*; 2002; vol. 11, pp. 1779-1787.
Ruiz et al. "IMGT, the International ImMunoGeneTics database", *Nucleic Acids Res.*, vol. 28, pp. 219-221 (2000).
Shiroguchi et al. "Digital RNA sequencing minimizes sequence-dependent bias and amplification noise with optimized single-molecule barcodes", *PNAS*, vol. 109, No. 4, pp. 1347-1352 (2012).
Smith et al., "Highly-multiplexed barcodes sequencing: an efficient methods for parallel analysis of pooled samples", Nucleic Acids Research, vol. 38, No. 13, pp. e142, 7 pages (2010).

\* cited by examiner

*Primary Examiner* — Changhwa J Cheu
(74) *Attorney, Agent, or Firm* — Kilpatrick Townsend & Stockton LLP (57) ABSTRACT

Compositions, methods, articles of manufacture, and kits are provided for storage and delivery of proteins.

18 Claims, 5 Drawing Sheets

Ab alone　　　　　　　　　Ab　Cyclodextrin wetting of porous paper　　　wetting of porous paper The presence of cyclodextrins in the Ab solution, inhibits the formation of Ab aggregates that form due to the wetting of the Ab solution in the porous paper. This results in:

Increased delivery of non-aggregated antibody

As well as a decrease in the residual amount of Ab left in the porous paper, post electrophoresis residual Ab left in porous paper after delivery more complete removal of Ab after delivery

ENHANCED FUNCTIONALITY AND DELIVERY OF A PROTEIN FROM A POROUS SUBSTRATE

CROSS-REFERENCE TO RELATED APPLICATION

This application is a divisional of U.S. application Ser. No. 14/340,364 filed Jul. 24, 2014, which claims priority to U.S. Provisional Application No. 61/858,488, filed Jul. 25, 2013, the contents of both of which are hereby incorporated by reference in their entireties for all purposes.

BACKGROUND OF THE INVENTION

During storage, a biomolecule should resist aggregation, denaturation, and degradation in order to remain stable. Biomolecules exhibit highly variable stability depending on the relative purity of the biomolecules, the identity of any contaminating biomolecules, the primary, secondary, and tertiary structure of the biomolecules, and the environment in which they are stored.

Methods of storage include precipitation and/or crystallization of the biomolecule. For example, biomolecules (e.g., proteins) may be precipitated and/or crystallized by a precipitant such as ammonium sulfate and stored for later reconstitution. Alternatively, biomolecules can be lyopholized and stored in a solid form. As yet another alternative, biomolecules can be stored in solution, such as in a buffered solution. Biomolecules that have been stored in a suitable manner, such that the biomolecule (or a substantial fraction thereof) is stable, can then be delivered from the storage medium, or extracted, and subsequently utilized for a variety of purposes.

BRIEF SUMMARY OF THE INVENTION

In some embodiments, the present invention provides a method of delivering a protein, the method comprising: providing a porous substrate comprising a reversibly immobilized protein and a protein aggregation modifying agent; and eluting the reversibly immobilized protein from the porous substrate with an eluent, thereby delivering the protein.

In some cases, the eluent comprises a buffered solution at a pH above the isoelectric point of the reversibly immobilized protein. In some cases, the eluent comprises a protein aggregation modifying agent selected from the group consisting of a cyclodextrin, a non-ionic surfactant, an ionic surfactant, a zwitterionic surfactant, a non-detergent sulfobetaine, a simple sugar, a polysaccharide, a polyol, an organic solvent, an aggregation modifying protein, a disordered peptide sequence, an amino acid, an oxido-reduction agent, a lyoprotectant, a cryoprotectant, and a chaotropic agent. In some cases, the eluent comprises a western blot transfer buffer. The western blot transfer buffer can contain tris(hydroxymethyl)aminomethane (Tris), N-cyclohexyl-3-aminopropanesulfonic acid (CAPS), glycine, methanol, ethanol, or propanol. The western blot transfer buffer can contain two or more compounds selected from the group consisting of tris-(hydroxymethyl)-aminomethane (Tris), N-cyclohexyl-3-aminopropanesulfonic acid (CAPS), glycine, methanol, ethanol, and propanol.

In some cases, the eluting comprises subjecting the substrate to diffusion, capillary action, vacuum, pressure, or electrophoresis, or contacting the porous substrate with a magnetic particle that has an affinity for the reversibly immobilized protein. In some cases, the eluting comprises eluting a portion of the protein onto a membrane. In some cases, the method comprises eluting at least 50% of the reversibly immobilized protein from the porous substrate with an eluent. In some cases, the method comprises eluting substantially all of the reversibly immobilized protein from the porous substrate with an eluent. In some cases, the eluted reversibly immobilized protein is less aggregated in comparison to a protein eluted from a porous substrate that does not comprise a protein aggregation modifying agent.

In some cases, the membrane has an immobilized protein on its surface. In some cases, the non-specific binding sites on the membrane are blocked. In some cases, the eluting comprises contacting the substrate with the membrane and transferring the protein reversibly immobilized on the substrate to the membrane via diffusion, capillary action, vacuum, pressure, or the application of an electromagnetic force. In some cases, the method further comprises washing non-specifically bound and unbound eluted protein from the membrane. In some cases, the method further comprises detecting the presence of the eluted protein on the membrane.

In some cases, the method further comprises binding the protein eluted from the substrate to the immobilized protein on the membrane surface; and detecting the presence of the eluted protein on the membrane, thereby detecting the presence of the immobilized protein on the membrane surface. In some cases, 1, 2, 3, 4 or more different proteins are reversibly immobilized on the porous substrate. In some cases, 1, 2, 3, 4 or more different proteins are reversibly immobilized on 1, 2, 3, 4, or more regions, e.g., laterally delimited regions, of the porous substrate.

In some cases, the porous substrate comprises a composition selected from the group consisting of whatman paper, paper, a cellulose filter, a glass microfiber filter, nitrocellulose, polyvinylidene difluoride, a sintered glass, a sintered polymer, a sintered metal, a spunbound polyester, rayon, nylon, a porous polymer monolith, a porous polymer bead, a capillary wicking bed, natural or synthetic sponge, and fiberglass. In some cases, the capillary wicking bed is a thin-film chromatography plate.

In some cases, the porous substrate comprises a mask region and a reversible immobilization region, wherein reversibly immobilized protein is immobilized on the reversible immobilization region. In some cases, the reversibly immobilized protein is reversibly immobilized across at least 30%, 40%, 50%, 60%, 70%, 80%, 90%, 95%, 99%, all, or substantially all of the reversible immobilization region. In some cases, the porous substrate further comprises 2, 3, 4 or more reversible immobilization regions. In some cases, the porous substrate further comprises a border region. In some cases, the mask region comprises a hydrophobic polymer. In some cases, the mask region comprises a fatty acid or wax. In some cases, the reversibly immobilized protein is evenly distributed across at least 30%, 40%, 50%, 60%, 70%, 80%, 90%, 95%, 99%, substantially all, or all of at least one surface of the substrate.

In some cases, the reversibly immobilized protein is reversibly immobilized on the porous substrate for less than about 12 hours, 24 hours, 48 hours, or less than about 1 week. In some cases, the protein is reversibly immobilized on the porous substrate for at least about 1 week, 1 month, 3 months, 6 months, 9 months, or 1 year.

In some cases, the reversibly immobilized protein is an antibody. In some cases, the antibody is reversibly immobilized on the porous substrate and no other antibody is immobilized on the porous substrate. In some cases, less than 50%, 40%, 30%, 20%, 10%, 5%, 2%, 1%, substantially no, or no protein is irreversibly immobilized on the porous substrate. In some cases, at least 50%, 60%, 70%, 80%, 90%, 95%, 99%, substantially all, or all of the reversibly immobilized protein is non-aggregated and non-denatured. In some cases, the reversibly immobilized protein is unlabeled. In some cases, the reversibly immobilized protein is labeled.

In some cases, the protein aggregation modifying agent is selected from the group consisting of a cyclodextrin, a non-ionic surfactant, an ionic surfactant, a zwitterionic surfactant, a non-detergent sulfobetaine, a simple sugar, a polysaccharide, a polyol, an organic solvent, an aggregation modifying protein, a disordered peptide sequence, an amino acid, an oxido-reduction agent, a lyoprotectant, a cryoprotectant, and a chaotropic agent.

The cyclodextrin can be selected from the group consisting of α-cyclodextrin, β-cyclodextrin, γ-cyclodextrin, (2,3,6-tri-O-methyl)-β-cyclodextrin, (2,3,6-tri-O-methyl)-β-cyclodextrin, (2-hydroxy)propyl-β-cyclodextrin, (2-hydroxy) propyl-γ-cyclodextrin, random methyl-β-cyclodextrin, random methyl-γ-cyclodextrin, carboxymethyl-β-cyclodextrin, carboxymethyl-γ-cyclodextrin, 6-monodeoxy-6-monoamino-β-cyclodextrin, sulfobutyl-β-cyclodextrin, 6-amino-6-deoxy-β-cyclodextrin, acetyl β-cyclodextrin, succinyl α-cyclodextrin, succinyl β-cyclodextrin, succinyl γ-cyclodextrin, (2,3,6-tri-O-benzoyl)-β-cyclodextrin, succinyl-(2-hydroxypropyl)-β-cyclodextrin, and succinyl-(2-hydroxypropyl)-γ-cyclodextrin.

The ionic surfactant can be sodium dodecyl sulfate or sodium octyl sulfate. The non-ionic surfactant can be selected from the group consisting of polysorbate 80, polysorbate 20, Brij-35, and a polyoxypropylene-polyoxyethylene block co-polymer. The non-detergent sulfobetaine can be selected from the group consisting of NDSB 256, NDSB 221, NDSB 211, NDSB 201, NDSB 195, 3-(4-tert-Butyl-1-pyridinio)-1-propanesulfonate, 3-(1-pyridinio)-1-propanesulfonate, 3-(Benzyldimethylammonio) propanesulfonate, and Dimethylethylammoniumpropane sulfonate. The simple sugar can be selected from the group consisting of sucrose, mannitol, sorbitol, inositol, xylitol, erythritol, glucose, galactose, raffinose, and trehalose. The polysaccharide can be selected from the group consisting of dextran, starch, and hydroxyethyl starch. The polyol can be selected from the group consisting of glycerol, ethylene glycol, polyethylene glycol, pentaerythritol propoxylate, and pentaerythritol propoxylate. The organic solvent can be selected from the group consisting of ethanol, butanol, propanol, dimethyl formamide, 2-methyl-2,4-pentanediol, 2,3-butanediol, 1,2-propanediol, 1,6-hexanediol, and dimethyl sulfoxide. The aggregation modifying protein can be selected from the group consisting of albumin, casein, gelatin, ubiquitin, lysozyme, and a late embryogenesis abundant (LEA) protein. The amino acid can be selected from the group consisting of glycine, proline, taurine, arginine, cystine, and cysteine. The oxido-reduction agent can be selected from the group consisting of mercaptoethanol, dithiothreitol, dithioerythriotl, tris(2-carboxyethyl)phosphine, glutathione, glutathione disulfide, and $Cu^{2+}$. And the lyoprotectant, cryoprotectant, or chaotropic agent can be selected from the group consisting of urea, thiourea, guanidinium, calcium, bromide, iodide, chloride, potassium, thiocyanate, perchlorate, chlorate, trimethylamine N-oxide, and phenol.

In some embodiments, the present invention provides a method of storing a protein the method comprising: providing a porous substrate and a protein aggregation modifying agent; contacting the porous substrate in the presence of the protein aggregation modifying agent with a solution containing a protein; and reversibly immobilizing the protein on the porous substrate, thereby storing the reversibly immobilized protein on the porous substrate.

In some cases, at least 50% of the reversibly immobilized protein is substantially non-denatured and substantially non-aggregated. In some cases, 1, 2, 3, or 4 or more different proteins are reversibly immobilized on the porous substrate. In some cases, the porous substrate comprises a composition selected from the group consisting of whatman paper, paper, a cellulose filter, a glass microfiber filter, nitrocellulose, polyvinylidene difluoride, a sintered glass, a sintered polymer, a sintered metal, a spunbound polyester, rayon, nylon, a porous polymer monolith, a porous polymer bead, a capillary wicking bed, natural or synthetic sponge, and fiberglass. In some cases, the capillary wicking bed is a thin-film chromatography plate.

In some cases, the porous substrate comprises a mask region, and a reversible immobilization region, wherein the method comprises reversibly immobilizing the protein on the reversible immobilization region. In some cases, the reversibly immobilized protein is reversibly immobilized across at least 30%, 40%, 50%, 60%, 70%, 80%, 90%, 95%, 99%, or substantially all of the reversible immobilization region. In some cases, the mask region comprises a hydrophobic polymer. In some cases, the mask region comprises a fatty acid or wax. In some cases, the porous substrate further comprises a border region. In some cases, the reversibly immobilized protein is evenly distributed across at least 30%, 40%, 50%, 60%, 70%, 80%, 90%, 95%, 99%, or all of at least one surface of the substrate.

In some cases, the reversible immobilization comprises drying the porous substrate after contacting the porous substrate in the presence of the protein aggregation modifying agent with the solution containing the protein. In some cases, the drying comprises air drying, vacuum drying, drying in an oven at 30, 40, 50, 60, or 65° C., or lyophilization. In some cases, the protein aggregation modifying agent substantially protects the reversibly immobilized protein from aggregation and denaturation during the drying. In some cases, the reversibly immobilized protein is stored on the porous substrate for at least about 1 week, 1 month, or 6 months. In some cases, the reversibly immobilized protein is stored on the porous substrate for less than about 12 hours, 24 hours, 48 hours, or 1 week.

In some cases, the protein is an antibody. In some cases, the antibody is reversibly immobilized on the porous substrate and no other antibody is immobilized on the porous substrate. In some cases, 2, 3, or 4 or more antibodies are reversibly immobilized on the porous substrate. In some cases, substantially no protein is irreversibly immobilized on the porous substrate. In some cases, the protein is unlabeled. In some cases, the protein is labeled.

In some cases, the porous substrate is configured to elute the reversibly immobilized protein when contacted with an eluent. In some cases, the contacting the porous substrate in the presence of the protein aggregation modifying agent with a solution containing a protein comprises contacting the solution containing the protein with a porous substrate that contains a protein aggregation modifying agent. In some cases, the contacting the porous substrate in the presence of the protein aggregation modifying agent with a solution containing a protein comprises contacting the porous substrate with a solution containing a protein and a protein aggregation modifying agent.

In some cases, the protein aggregation modifying agent is selected from the group consisting of a cyclodextrin, a non-ionic surfactant, an ionic surfactant, a zwitterionic surfactant, a non-detergent sulfobetaine, a simple sugar, a polysaccharide, a polyol, an organic solvent, an aggregation modifying protein, a disordered peptide sequence, an amino acid, an oxido-reduction agent, a lyoprotectant, a cryoprotectant, and a chaotropic agent.

The cyclodextrin can be selected from the group consisting of α-cyclodextrin, β-cyclodextrin, γ-cyclodextrin, (2,3, 6-tri-O-methyl)-β-cyclodextrin, (2,3,6-tri-O-methyl)-β-cyclodextrin, (2-hydroxy)propyl-β-cyclodextrin, (2-hydroxy) propyl-γ-cyclodextrin, random methyl-β-cyclodextrin, random methyl-γ-cyclodextrin, carboxymethyl-β-cyclodextrin, carboxymethyl-γ-cyclodextrin, 6-monodeoxy-6-monoamino-β-cyclodextrin, sulfobutyl-β-cyclodextrin, 6-amino-6-deoxy-β-cyclodextrin, acetyl β-cyclodextrin, succinyl α-cyclodextrin, succinyl β-cyclodextrin, succinyl γ-cyclodextrin, (2,3,6-tri-O-benzoyl)-β-cyclodextrin, succinyl-(2-hydroxypropyl)-γ-cyclodextrin, and succinyl-(2-hydroxypropyl)-γ-cyclodextrin.

The ionic surfactant can be sodium dodecyl sulfate or sodium octyl sulfate. The non-ionic surfactant can be selected from the group consisting of polysorbate 80, polysorbate 20, Brij-35, and a polyoxypropylene-polyoxyethylene block co-polymer. The non-detergent sulfobetaine can be selected from the group consisting of NDSB 256, NDSB 221, NDSB 211, NDSB 201, NDSB 195, 3-(4-tert-Butyl-1-pyridinio)-1-propanesulfonate, 3-(1-pyridinio)-1-propanesulfonate, 3-(Benzyldimethylammonio) propanesulfonate, and Dimethylethylammoniumpropane sulfonate. The simple sugar can be selected from the group consisting of sucrose, mannitol, sorbitol, inositol, xylitol, erythritol, glucose, galactose, raffinose, and trehalose. The polysaccharide can be selected from the group consisting of dextran, starch, and hydroxyethyl starch. The polyol can be selected from the group consisting of glycerol, ethylene glycol, polyethylene glycol, pentaerythritol propoxylate, and pentaerythritol propoxylate. The organic solvent can be selected from the group consisting of ethanol, butanol, propanol, dimethyl formamide, 2-methyl-2,4-pentanediol, 2,3-butanediol, 1,2-propanediol, 1,6-hexanediol, and dimethyl sulfoxide. The aggregation modifying protein can be selected from the group consisting of albumin, casein, gelatin, ubiquitin, lysozyme, and a late embryogenesis abundant (LEA) protein. The amino acid can be selected from the group consisting of glycine, proline, taurine, arginine, cystine, and cysteine. The oxido-reduction agent can be selected from the group consisting of mercaptoethanol, dithiothreitol, dithioerythritol, tris(2-carboxyethyl)phosphine, glutathione, glutathione disulfide, and $Cu^{2+}$. The lyoprotectant, cryoprotectant, or chaotropic agent can be selected from the group consisting of urea, thiourea, guanidinium, calcium, bromide, iodide, chloride, potassium, thiocyanate, perchlorate, chlorate, trimethylamine N-oxide, and phenol.

In some embodiments, the present invention provides an article of manufacture comprising a porous substrate, a protein reversibly immobilized on a surface of the substrate, and a protein aggregation modifier, wherein the article is made by any of the foregoing methods. In some cases, the protein reversibly immobilized on the surface of the substrate is dry. In some cases, the substrate is at least about 5-15 cm wide and at least about 5-15 cm long.

In some embodiments, the present invention provides a kit comprising any of the foregoing articles of manufacture and an elution buffer. In some cases, the elution buffer comprises a protein aggregation modifier selected from the group consisting of a cyclodextrin, a non-ionic surfactant, an ionic surfactant, a zwitterionic surfactant, a non-detergent sulfobetaine, a simple sugar, a polysaccharide, a polyol, an organic solvent, an aggregation modifying protein, a disordered peptide sequence, an amino acid, an oxido-reduction agent, a lyoprotectant, a cryoprotectant, and a chaotropic agent. In some cases, the elution buffer comprises a western blot transfer buffer.

In some embodiments, the present invention provides a kit comprising a package of at least 2, 3, 4, 5, 6, 7, 8, 9, 10, or more of any of the foregoing articles of manufacture.

In some embodiments, the present invention provides a system for delivering protein comprising: any of the foregoing articles of manufacture; a membrane having a second protein immobilized on a surface; a transfer buffer; and an apparatus adapted to transfer the reversibly immobilized protein on the substrate to the membrane via diffusion, capillary action, vacuum, pressure, or electromagnetic force.

DETAILED DESCRIPTION OF THE INVENTION

I. Definitions

The term "reversibly immobilized" as used herein refers to a biomolecule (e.g., a protein) that has been immobilized on a substrate (e.g., a porous substrate) such that it can be eluted from the substrate. The reversibly immobilized biomolecule can be immobilized such that it can be eluted without loss of activity (e.g., binding or enzymatic activity), or without substantial loss of activity (e.g., retains at least 30%, 40%, 50%, 60%, 70%, 80%, 90%, 95%, 99%, all, or substantially all of its binding or enzymatic activity prior to reversible immobilization). For example, the reversibly immobilized biomolecule can be immobilized such that at least 30%, 40%, 50%, 60%, 70%, 80%, 90%, 95%, 99%, all, or substantially all of the biomolecule can be eluted from the substrate in a non-denatured or non-aggregated form.

The term "amino acid" refers to naturally occurring and synthetic amino acids, as well as amino acid analogs and amino acid mimetics that function similarly to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs may have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions similarly to a naturally occurring amino acid.

Amino acids may be referred to herein by either their commonly known three letter symbols or by the one-letter symbols recommended by the IUPAC-IUB Biochemical Nomenclature Commission.

The term "western blot" includes not only the standard western blot, but also variants such as far-western blot, Northwestern blot and Southwestern blot. In general, a western blot involves the transfer of a protein to a membrane, and subsequent detection of the protein on the membrane. There are a variety of membranes suitable for use as western blot membranes known in the art including, without limitation, polyvinylidene difluoride (PVDF) membrane, nitrocellulose membrane, polyamide membrane, polyester membrane, and nylon membrane. Western blotting typically utilizes a transfer buffer. There are a variety of western blot transfer buffers known in the art. In general, the western blot transfer buffer will have a pH that is above the isoelectric point of the protein to be transferred. Thus, when a voltage potential is applied, the protein will migrate toward the positive electrode. Alternatively, the transfer buffer can have a pH below the isoelectric point of the protein to be transferred. In such cases, the protein will migrate toward the negative electrode.

As used herein, an "antibody" refers to a protein functionally defined as a binding protein and structurally defined as comprising an amino acid sequence that is recognized by one of skill as being derived from the framework region of an immunoglobulin-encoding gene of an animal that produces antibodies. An antibody can consist of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains, respectively.

The term "antibody" as used herein also includes antibody fragments that retain binding specificity. For example, there are a number of well characterized antibody fragments. Thus, for example, pepsin digests an antibody C-terminal to the disulfide linkages in the hinge region to produce F(ab')2, a dimer of Fab which itself is a light chain joined to VH-CH1 by a disulfide bond. The F(ab')2 may be reduced under mild conditions to break the disulfide linkage in the hinge region thereby converting the (Fab')2 dimer into a Fab' monomer. The Fab' monomer is essentially an Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that fragments can be synthesized de novo by utilizing recombinant DNA methodology or chemically. Thus, the term "antibody", as used here includes antibody fragments either produced by the modification of whole antibodies or synthesized using recombinant DNA methodologies.

Antibodies as used here also include various $V_H$-$V_L$ pair formats, including single chain antibodies (antibodies that exist as a single polypeptide chain), e.g., single chain Fv antibodies (sFv or scFv), in which a variable heavy and a variable light region are joined together (directly or through a peptide linker) to form a continuous polypeptide. The single chain Fv antibody is a covalently linked $V_H$-$V_L$ that may be expressed from a nucleic acid including $V_H$- and $V_L$-encoding sequences either joined directly or joined by a peptide-encoding linker (e.g., Huston, et al. *Proc. Nat. Acad. Sci. USA*, 85:5879-5883, 1988). While the $V_H$ and $V_L$ are connected to each as a single polypeptide chain, the $V_H$ and $V_L$ domains associate non-covalently. An antibody can also be in another fragment form, such as a disulfide-stabilized Fv (dsFv). Other fragments can also be generated, e.g., using recombinant techniques, as soluble proteins or as fragments obtained from display methods. Antibodies can also include diantibodies and miniantibodies.

Antibodies of the invention also include heavy chain dimers, such as antibodies from camelids or sharks. Since the $V_H$ region of a heavy chain dimer IgG in a camelid or shark does not have to make hydrophobic interactions with a light chain, the region in the heavy chain that normally contacts a light chain is changed to hydrophilic amino acid residues. $V_H$ domains of heavy-chain dimer IgGs are called VHH (camelid) or VNAR (shark) domains. Antibodies for use in the current invention additionally include single domain antibodies (dAbs) and nanobodies (see, e.g., Cortez-Retamozo, et al., *Cancer Res.* 64:2853-2857, 2004).

II. Introduction

Proteins can be stored and delivered in a variety of ways. For example, proteins may be stored in a solution, as a lyophilized solid, or immobilized onto a substrate. In any case, it is desirable to employ storage and delivery conditions that protect the stability of the protein. For example, proteins are generally stored in a manner that reduces protein denaturation and aggregation. Protein denaturation or aggregation can be induced by a variety of phenomenon including heat, cold, ionic strength, pH, the presence of a denaturant, and contact with a hydrophobic interface. One of the most hydrophobic interfaces is the air water interface. Consequently, it is generally desirable to reduce protein aggregation during storage and delivery by minimizing contact with air-water interfaces.

During protein storage and delivery, a protein can encounter an air water interface at many points. For example, protein aggregation can be induced by contact with an air water interface during mixing or pipetting of a protein. Similarly, protein aggregation can be induced by contact with an air water interface simply while residing in a container as a protein solution. In particular, storage mechanisms in which a protein is contacted with a solid surface substrate can introduce an extremely large air-water interface. For example, a protein in solution that is contacted with a substrate will be subject to an increasingly large air water interface to volume ratio as the volume of the liquid in which the protein is solubilized decreases during the drying step.

Similarly, a protein dried onto a substrate can experience aggregation during a subsequent rewetting step, such as prior to, or during, delivery of the stored protein. For example, as the substrate is contacted with a wetting solution (e.g., an eluent), there will exist a large air-water interface. As explained above, interaction between the protein and the air-water interface can lead to protein denaturation and/or aggregation. Porous substrates in particular exacerbate this air-water interface problem because the interstitial spaces of the substrate lead to a large air-water interface.

The inventors have discovered that aggregation of a protein on a substrate (e.g., a porous substrate) can be surprisingly reduced or eliminated by the presence of protein aggregation modifying agents. Without wishing to be bound by theory, it is believed that protein aggregation modifying agents that act to displace proteins from the air-water interface, and thereby protect them from denaturation and aggregation, are particularly effective in reducing the aggregation of proteins immobilized on a porous substrate.

Accordingly, described herein are methods and compositions for storing proteins on and/or within a porous substrate and delivering such proteins under conditions that reduce or eliminate aggregation or denaturation. Such conditions include the use of one or more protein aggregation modifying agents as described herein. Also provided herein are compositions containing a protein stored on a porous substrate such that the protein is protected from aggregation or denaturation by the presence of a protein aggregation modifying agent. Also described herein are kits containing multiple compositions containing a protein stored on a porous substrate. Such compositions and kits can, e.g., be used to deliver a protein to a membrane, a container, or other assay platform for subsequent analysis. The specification also describes kits for storing proteins on a porous substrate in the presence of a protein aggregation modifying agent.

III. Compositions

Described herein are compositions containing a porous substrate, a protein, and a protein aggregation modifying agent for storage or delivery of the protein.

A. Proteins

The protein to be stored or delivered can be any protein. For example, the protein can be an antibody, an affimer, a lipocalin (e.g., an anticalin), thioredoxin A, bilin binding protein, or a protein containing an ankyrin repeat, the Z domain of staphylococcal protein A, or a fibronectin type III domain. The protein can also be an enzyme, a reporter protein, a receptor, a hormone, a toxin, a cytokine, or a detection reagent. The protein can be labeled or unlabeled as described herein. The protein can be purified from a biological source or synthesized. For example, the protein can be produced in a cell, e.g., heterologously produced in a cell and purified therefrom. In some cases, the protein is a recombinant protein.

In some embodiments, the protein can be a polypeptide containing at least 10-15 amino acids. Such a polypeptide can be purified from a biological source or produced by synthetic methods. Alternatively, the protein can be a longer polypeptide, e.g., at least 15, 20, 25, 30, 35, 40, 50, 60, 70, 80, 90, or 100 amino acids. For example, the polypeptide can be between 15-20, 20-30, 30-40, 40-50, 50-60, 60-70, 80-90, or 90-100 amino acids in length. In some embodiments, the protein can be at least about 100, 150, 200, 250, 300, 400, 500, 600, 700, 800, 900, 1000, 1250, 1500, 2000, 2500, 3000, 5000 amino acids in length or more.

In some embodiments, the protein can be a protein fragment. For example, the protein can consist of a one or more domains of a larger protein. In some cases, the protein can consist of a fragment that contains the desired activity. For example, the protein can consist of a fragment that contains a binding or enzymatic activity.

Labels

The proteins described herein can be detected by detecting a label that is linked to the protein. The label can be linked directly to the protein (e.g., by a covalent bond) or the attachment can be indirect (e.g., using a chelator or linker molecule). The terms "label" and "detectable label" are used synonymously herein. In some embodiments, each protein label (e.g., a first label linked to a first protein, a second label linked to a second protein, etc.) generates a detectable signal and the signals (e.g., a first signal generated by the first label, a second signal generated by the second label, etc.) are distinguishable. In some embodiments, the two or more protein labels comprise the same type of agent (e.g., a first label that is a first fluorescent agent and a second label that is a second fluorescent agent). In some embodiments, the two or more protein labels (e.g., the first label, second label, etc.) combine to produce a detectable signal that is not generated in the absence of one or more of the labels.

Examples of detectable labels include, but are not limited to, biotin/streptavidin labels, nucleic acid (e.g., oligonucleotide) labels, chemically reactive labels, fluorescent labels, enzyme labels, radioactive labels, quantum dots, polymer dots, mass labels, and combinations thereof. In some embodiments, the label can include an optical agent such as a chromophore, fluorescent agent, phosphorescent agent, chemiluminescent agent, etc. Numerous agents (e.g., dyes, probes, or indicators) are known in the art and can be used in the present invention. (See, e.g., Invitrogen, The Handbook—A Guide to Fluorescent Probes and Labeling Technologies, Tenth Edition (2005)). Chromophores include coenzymes or co-factors that have a detectable absorbance. In some cases, a protein can be detected by detecting the intrinsic absorbance of a peptide bond at, e.g., 220 or 280 nm.

Fluorescent agents can include a variety of organic and/or inorganic small molecules or a variety of fluorescent proteins and derivatives thereof. For example, fluorescent agents can include but are not limited to cyanines, phthalocyanines, porphyrins, indocyanines, rhodamines, phenoxazines, phenylxanthenes, phenothiazines, phenoselenazines, fluoresceins (e.g., FITC, 5-carboxyfluorescein, and 6-carboxyfluorescein), benzoporphyrins, squaraines, dipyrrolo pyrimidones, tetracenes, quinolines, pyrazines, corrins, croconiums, acridones, phenanthridines, rhodamines (e.g., TAMRA, TMR, and Rhodamine Red), acridines, anthraquinones, chalcogenopyrylium analogues, chlorins, naphthalocyanines, methine dyes, indolenium dyes, azo compounds, azulenes, azaazulenes, triphenyl methane dyes, indoles, benzoindoles, indocarbocyanines, benzoindocarbocyanines, BODIPY™ and BODIPY™ derivatives, and analogs thereof. In some embodiments, a fluorescent agent is an Alexa Fluor dye. In some embodiments, a fluorescent agent is a polymer dot or a quantum dot. Fluorescent dyes and fluorescent label reagents include those which are commercially available, e.g., from Invitrogen/Molecular Probes (Eugene, Oreg.) and Pierce Biotechnology, Inc. (Rockford, Ill.). In some embodiments, the optical agent is an intercalating dye. In some embodiments, 2, 3, 4, 5, or more proteins are each labeled with an optical agent such as a fluorescent agent (e.g., a first protein labeled with a first fluorescent label, a second protein labeled with a second fluorescent label, etc.), and each protein that is labeled with an optical agent is detected by detecting a signal generated by the optical agent (e.g., a fluorescent signal generated by a fluorescent label). In some embodiments, all of the proteins are labeled with an optical agent, and each optical agent-labeled protein is detected by detecting a signal generated by the optical agent.

In some embodiments, the label is a radioisotope. Radioisotopes include radionuclides that emit gamma rays, positrons, beta and alpha particles, and X-rays. Suitable radionuclides include but are not limited to $^{225}$Ac, $^{72}$As, $^{211}$At, $^{11}$B, $^{128}$Ba, $^{212}$Bi, $^{75}$Br, $^{77}$Br, $^{14}$C, $^{109}$Cd, $^{62}$Cu, $^{64}$Cu, $^{67}$Cu, $^{18}$F, $^{67}$Ga, $^{68}$Ga, $^{3}$H, $^{166}$Ho, $^{123}$I, $^{124}$I, $^{125}$I, $^{130}$I, $^{131}$I, $^{111}$In, $^{177}$Lu, $^{13}$N, $^{15}$O, $^{32}$P, $^{33}$P, $^{212}$Pb, $^{103}$Pd, $^{186}$Re, $^{188}$Re, $^{47}$Sc, $^{153}$Sm, $^{89}$Sr, $^{99m}$Tc, $^{88}$Y and $^{90}$Y. In some embodiments, 2, 3, 4, 5 or more proteins are each labeled with a radioisotope (e.g., a first protein labeled with a first radioisotope, a second protein labeled with a second radioisotope, etc.), and each protein that is labeled with a radioisotope is detected by detecting radioactivity generated by the radioisotope. For example, one protein can be labeled with a gamma emitter and one protein can be labeled with a beta emitter. Alternatively, the proteins can be labeled with radionuclides that emit the same particle (e.g., alpha, beta, or gamma) at different energies, where the different energies are distinguishable. In some embodiments, all of the proteins are labeled with a radioisotope and each labeled protein can be detected by detecting radioactivity generated by the radioisotope.

In some embodiments, the label is an enzyme, and the protein is detected by detecting a product generated by the enzyme. Examples of suitable enzymes include, but are not limited to, urease, alkaline phosphatase, (horseradish) hydrogen peroxidase (HRP), glucose oxidase, β-galactosidase, luciferase, alkaline phosphatase, and an esterase that hydrolyzes fluorescein diacetate. For example, a horseradish-peroxidase detection system can be used with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, which yields a soluble product readily detectable at 405 nm. A β-galactosidase detection system can be used with the chromogenic substrate o-nitrophenyl-β-D-galactopyranoside (ONPG), which yields a soluble product detectable at 410 nm. A urease detection system can be used with a substrate such as urea-bromocresol purple (Sigma Immunochemicals; St. Louis, Mo.). In some embodiments, 2, 3, 4, 5, or more proteins are each labeled with an enzyme (e.g., a first protein labeled with a first enzyme, a second protein labeled with a second enzyme, etc.), and each protein that is labeled with an enzyme is detected by detecting a product generated by the enzyme. In some embodiments, all of the proteins are labeled with an enzyme, and each enzyme-labeled protein is detected by detecting a product generated by the enzyme.

In some embodiments, the label is an affinity tag. Examples of suitable affinity tags include, but are not limited to, biotin, peptide tags (e.g., FLAG-tag, HA-tag, His-tag, Myc-tag, S-tag, SBP-tag, Strep-tag, eXact-tag), and protein tags (e.g., GST-tag, MBP-tag, GFP-tag).

In some embodiments, the label is a nucleic acid label. Examples of suitable nucleic acid labels include, but are not limited to, oligonucleotide sequences, single-stranded DNA, double-stranded DNA, RNA (e.g., mRNA or miRNA), or DNA-RNA hybrids. In some embodiments, the nucleic acid label is about 10, 15, 20, 25, 30, 35, 40, 45, 50, 60, 70, 80, 90, 100, 150, 200, 250, 300, 350, 400, 450, 500, 600, 700, 800, 900, or 1000 nucleotides in length.

In some embodiments, the label is a nucleic acid barcode. As used herein a "barcode" is a short nucleotide sequence (e.g., at least about 4, 6, 8, 10, or 12, nucleotides long) that uniquely defines a labeled molecule, or a second molecule bound to the labeled protein. The length of the barcode sequence determines how many unique samples can be differentiated. For example, a 4 nucleotide barcode can differentiate 44 or 256 samples or less, a 6 nucleotide barcode can differentiate 4096 different samples or less, and an 8 nucleotide barcode can index 65,536 different samples or less. The use of barcode technology is well known in the art, see for example Katsuyuki Shiroguchi, et al. Digital RNA sequencing minimizes sequence-dependent bias and amplification noise with optimized single-molecule barcodes, PNAS (2012); and Smith, A M et al. Highly-multiplexed barcode sequencing: an efficient method for parallel analysis of pooled samples, Nucleic Acids Research Can 11, (2010).

In some embodiments, the label is a "click" chemistry moiety. Click chemistry uses simple, robust reactions, such as the copper-catalyzed cycloaddition of azides and alkynes, to create intermolecular linkages. For a review of click chemistry, see Kolb et al., *Agnew Chem* 40:2004-2021 (2001). In some embodiments, a click chemistry moiety (e.g., an azide or alkyne moiety) can be detected using another detectable label (e.g., a fluorescently labeled, biotinylated, or radiolabeled alkyne or azide moiety).

Techniques for attaching detectable labels to proteins are well known. For example, a review of common protein labeling techniques can be found in *Biochemical Techniques: Theory and Practice*, John F. Robyt and Bernard J. White, Waveland Press, Inc. (1987). Other labeling techniques are reviewed in, e.g., R. Haugland, Excited States of Biopolymers, Steiner ed., Plenum Press (1983); Fluorogenic Probe Design and Synthesis: A Technical Guide, PE Applied Biosystems (1996); and G. T. Herman, Bioconjugate Techniques, Academic Press (1996).

In some embodiments, two or more protein labels (e.g., a first label, second label, etc.) combine to produce a detectable signal that is not generated in the absence of one or more of the labels. For example, in some embodiments, each of the labels is an enzyme, and the activities of the enzymes combine to generate a detectable signal that is indicative of the presence of the labels (and thus, is indicative of each of the labeled proteins). Examples of enzymes combining to generate a detectable signal include coupled assays, such as a coupled assay using hexokinase and glucose-6-phosphate dehydrogenase; and a chemiluminescent assay for NAD (P)H coupled to a glucose-6-phosphate dehydrogenase, beta-D-galactosidase, or alkaline phosphatase assay. See, e.g., Maeda et al., *J Biolumin Chemilumin* 1989, 4:140-148.

B. Substrates

As described herein, a protein can be stored on, or delivered from, a substrate under conditions that reduce protein aggregation or denaturation. The protein can be stored on, or delivered from, any suitable substrate. In general, the substrate must be mechanically and chemically stable enough to provide a platform for protein storage and delivery. Also, the substrate compositions described herein generally provide for reversible immobilization of the protein such that at least 30%, 40%, 50%, 60%, 70%, 80%, 90%, 95%, 99%, all, or substantially all of the protein can be eluted from the substrate. In some cases, the substrate composition is selected so that all, substantially all, or at least 30%, 40%, 50%, 60%, 70%, 80%, 90%, 95%, or 99% of the protein remains free, substantially free, or at least 30%, 40%, 50%, 60%, 70%, 80%, 90%, 95%, or 99% free of aggregates.

The substrate can be any size and shape. For example, the substrate can be circular, oval, square, or rectangular. In some cases, the substrate is a rectangular strip, e.g., a chromatography strip. For example, the substrate can be a strip of about 0.25, 0.5, or 1 cm in width. In some cases, the strip can be used to deliver a protein to a region, a lane, or a number of lanes of a gel (e.g., a polyacrylamide gel) or a membrane (e.g., a nitrocellulose, PVDF, or nylon membrane). In general, the substrate will have three substantial dimensions (e.g., a measurable length, width, and thickness, or a measurable radius and thickness). In some cases, the substrate is roughly planar in that it has two dimensions (e.g., length and width) that are each at least about 2-fold, 5-fold, 10-fold, 100-fold, or more larger than the third dimension (e.g., thickness). In some cases, the substrate can be sized for use in a blotting apparatus, such as a Southern or western blotting apparatus. In some cases, the substrate is a membrane. Alternatively, the substrate can consist of one or more beads.

In some embodiments, the substrate is sized to provide for ease of manipulation by hand. In other embodiments, the substrate can be smaller than that which is readily manipulated by hand. For example, the substrate can be either larger than about 1 cm×1 cm in length and width (e.g., larger than about 2 cm in any dimension, or larger than about 5 cm in any dimension) and thus easy to handle. Alternatively, the substrate can be smaller than about 1 cm×1 cm (e.g., smaller than about 0.5 cm×0.5 cm or smaller than about 0.1 cm×0.1 cm) in length and width and thus suitable for micromanipulation techniques.

Exemplary sizes include substrates that are at least about 0.25 cm, 0.5 cm, 1 cm, 2 cm, 3 cm, 4 cm, 5 cm, 6 cm, 7 cm, 8 cm, 10 cm, 12 cm, 15 cm, 20 cm, 30 cm or more in at least one dimension. Exemplary sizes further include substrates that are about 1 cm×1 cm, 7×8.4 cm, 8.5×13.5 cm, 10 cm×15 cm, or 25×28 cm in length and width respectively. Exemplary sizes further include 8.5 cm×9 cm, 7 cm×9 cm, 8 cm×10.7 cm, 10 cm×10 cm, 7 cm×8.5 cm, 8.3 cm×7.3 cm, 8 cm×8 cm, 8.3 cm×13 cm, 10.8 cm×13.5 cm. In some cases, the substrate is configured to deliver protein to a microtiter plate (e.g., a 6, 8, 12, 24, 48, 96, 384, or 1536 well plate). For example, the substrate may be sized to the dimensions of such a microtiter plate. In some cases, the substrate is configured to deliver protein to a microscope slide, or a microarray. For example, the substrate may be sized to the dimensions of such a microtiter plate.

The substrate can be a porous substrate. Porous substrates generally have a large surface area due to the presence of a plurality of pores. The large surface area can increase the protein loading capacity of the substrate. In the absence of a protein aggregation modifier, however, the large surface area of the porous substrate can also increase protein aggregation due to the increased air-water interface.

In some embodiments, the porous substrate has a large surface area as compared to a nonporous substrate of the same material and size. For example, the porous substrate can have at least about a 2, 3, 4, 5, 6, 7, 8, 9, 10, 15, 20, 25, 30, 40, 50, 100, 200, 300, 500, 1000-fold or more increased surface area as compared to a nonporous substrate of the same material and size. In some embodiments, the porous substrate has a large surface specific surface area. For example, the porous substrate can have a specific surface area of at least about 0.1 m$^2$/g, 0.5 m$^2$/g, 1 m$^2$/g, 10 m$^2$/g, or more as measured by standard techniques.

In some embodiments, the porous substrate possesses a high specific binding capacity for protein. For example, in some cases, the porous substrate can immobilize at least about 0.1 mg, 0.5 mg, 1 mg, 5 mg, 10 mg, 15 mg, 20 mg, 40 mg, 60 mg, 100 mg, or more protein for every mg of substrate material.

In some embodiments, the porous substrate can have a particular pore size, a particular average pore size, or a particular pore size range. For example, the porous substrate can contain 0.1 µm pores, 0.2 µm pores, 0.45 µm pores, or 1, 2, 4, 5, 6, 7, 8, 10, 15, 20 µm pores, or pores larger than about 20 µm. As another example, the porous substrate can contain pores that average 0.1, 0.2, 0.45, 1, 2, 4, 5, 6, 7, 8, 10, 15, or 20 µm, or more in size. As another example, the porous substrate can contain pores that range about 0.1-8 µm, 0.2-8 µm, 0.45-8 µm, 1-8 µm, 0.1-4 µm, 0.1-2 µm, 0.1-1 µm, 0.1-0.45 µm, 0.2-8 µm, 0.2-4 µm, 0.2-2 µm, 0.2-1 µm, 0.2-0.45 µm, 0.45-8 µm, 0.45-4 µm, 0.45-2 µm, 0.45-1 µm in size. In some cases, the porous substrate can contain pores that are less than about 20 µm in size. For example, the porous substrate can consist of a material in which at least about 50%, 60%, 70%, 80%, 90% or more of the pores are less than about 20, 15, 10, or 5 µm in size. In some cases, the pores are large enough to contain one or more proteins of average size (e.g., about 1 nm). For example, the pores can be at least 1 nm in size, at least 5 nm in size, at least 10, 100, or 500 nm in size. Alternatively, at least 50%, 60%, 70%, 80%, 90% or more of the pores can be more than 1, 5, 10, 50, 100, or 500 nm in size. As used herein, pore size can be measured as a radius or a diameter.

The substrate can be treated or functionalized to provide higher protein loading, directed protein loading, or specificity for a particular protein. For example, the substrate, or a portion thereof, can be treated to alter the hydrophilicity or alter the hydrophobicity of the treated area. In some cases, altering the hydrophilicity or hydrophobicity of a substrate can increase protein loading, create mask regions in which protein is not loaded, direct flow of proteins when the substrate is wet, or reduce protein denaturation or aggregation.

In addition to mask regions in which the protein is not reversibly immobilized, the substrate can also contain a border region. In some cases, the border region is marked or annotated to provide orientation information or describe the type or nature of the reversibly immobilized protein. In some cases, the border region can be configured to provide a region for handling the substrate. For example, the border region can serve as a useful handle for manual or robotic manipulation of the substrate.

Mask regions and border regions, e.g., laterally delimited regions, are described, for example, in U.S. application Ser. No. 13/950,590 filed on Jul. 25, 2013, herein incorporated by reference in its entirety.

The substrate can be marked or annotated such that the origin, composition, or location of the reversibly immobilized protein is recorded. For example, one or more mask regions can be visually discernible, such that one of skill in the art can determine the location of the reversibly immobilized protein. Alternatively, the protein name, identity, amount, lot number, etc. can be printed or stamped on a portion of the substrate. In some cases, the substrate is marked or annotated such that the proper orientation for transfer, e.g., in a transfer apparatus, of the reversibly immobilized protein to a second substrate or a membrane is discernible.

As another example, the substrate, or a portion thereof, can be functionalized with a ligand to which a protein will bind or that will bind to a protein. Exemplary ligands include, but are not limited to, ligands which interact with antibodies, e.g., protein A, G, or L. Exemplary ligands also include polypeptide antigen tags, e.g., a myc, HA, FLAG, S, SBP, V5, Softag, Avitag, calmodulin, His, Xpress, TC, or Ty tag. One of skill in the art will recognize that a wide variety of ligands can be used herein, and the choice of a particular ligand will depend on the protein to be stored or delivered.

As yet another example, the substrate, or a portion thereof, can be functionalized to provide an ion exchange utility. For example, the substrate, or a portion thereof, can be functionalized to increase the binding of cations, anions, or cations and anions. Functional groups suitable for use in providing an ion exchange utility include tertiary and quaternary amines for soft and hard anion exchange respectively. Functional groups suitable for use in providing an ion exchange utility also include carboxylic acids and sulphonates for soft and hard cation exchange respectively.

Substrates include, but are not limited to, polymer containing substrates. The polymer can consist of polymer beads, a polymer membrane, or a polymer monolith. In some cases, the polymer is cellulose. Cellulose containing substrates include paper, cloth, woven, or non-woven cellulose substrates. Cloth substrates include those containing a natural cellulose fiber such as cotton or wool. Paper substrates include those containing natural cellulose fiber (e.g., cellulose or regenerated cellulose) and those containing cellulose fiber derivatives including, but not limited to cellulose esters (e.g., nitrocellulose, cellulose acetate, cellulose triacetate, cellulose proprionate, cellulose acetate propionate, cellulose acetate butyrate, and cellulose sulfate) and cellulose ethers (e.g., methylcellulose, ethylcellulose, ethyl methyl cellulose, hydroxyethyl cellulose, hydroxyethyl methyl cellulose, hydroxypropyl methyl cellulose, ethyl hydroxyethyl cellulose, and carboxymethyl cellulose). In some cases, the cellulose substrate contains rayon. In some cases, the substrate is paper, such as a variety of WHATMAN® paper.

Substrates further include substrates that contain a sintered material. For example, the substrate can contain a sintered glass, a sintered polymer, or sintered metal. In some cases, the sintered material is formed by sintering one or more of powdered glass, powdered polymer, or powdered metal. In other cases, the sintered material is formed by sintering one or more of glass, metal, or polymer fibers. In still other cases, the sintered material is formed from the sintering of one or more of glass, polymer, or metal beads.

Substrates can also contain one or more non-cellulosic polymers, e.g. a synthetic polymer, a natural polymer, or a semisynthetic polymer. For example, the substrate can contain a polyester, such as polyglycolide, polylactic acid, polycaprolactone, polyethylene adipate, polyhydroxylalkanoate, polyhydroxybutyrate, poly(3-hydroxybutyrate-co-3-hydroxyvalerate, polyethylene terephthalate, polybutylene terephthalate, polytrimethylene terephthalate, polyethylene naphthalate, Vectran®. In some cases, the polymer is spunbound, such as a spunbound polyester.

Additional synthetic polymers include, but are not limited to nylon, polypropylene, polyethylene, polystyrene, divinylbenzene, polyvinyl, polyvinyl difluoride, high density polyvinyl difluoride, polyacrylamide, a (C2-C6) monoolefin polymer, a vinylaromatic polymer, a vinylaminoaromatic polymer, a vinylhalide polymer, a (C1-C6) alkyl (meth) acrylate polymer, a(meth)acrylamide polymer, a vinyl pyrrolidone polymer, a vinyl pyridine polymer, a (C1-C6) hydroxyalkyl (meth)acrylate polymer, a (meth)acrylic acid polymer, an acrylamidomethylpropylsulfonic acid polymer, an N-hydroxy-containing (C1-C6) alkyl(meth)acrylamide polymer, acrylonitrile or a mixture of any of the foregoing.

Substrates can also contain one or more polysaccharides. Exemplary polysaccharides include those containing cellulose, agarose, amylose, chitin, chitosan, galactosamine, curdlan, dextran, xylan, inulin, and derivatives thereof, e.g., esters, phenyl carbamates, alkyl carabmates, and benzyl carbamates. In some cases, the polysaccharides are crosslinked. For example, the substrate can include agarose, or a cross linked agarose. In some cases, the substrate can include cross links between the polysaccharide and other constituents of the substrate.

Substrates also include capillary wicking beds and materials used therein. For example, the substrate can include a thin layer chromatography plate, or be formed of any of the thin layer chromatography substrates known in the art. Thin layer chromatography substrates known in the art include, but are not limited to, silica, silica derivatized with C4, C8, or C18 alkyl groups, and alumina.

Substrates can also contain glass, glass fibers, fiberglass, natural or synthetic sponge, silica, alumina, or a derivative thereof.

In addition to the foregoing substrate materials, the substrate can also contain any combination of the foregoing. In some cases, the substrate can contain composite materials that include a combination of materials described above. For example, the substrate can contain glass or silica fibers in a synthetic polymer matrix.

In some embodiments, the compositions described herein include substrates on which a protein is reversibly immobilized thereon. For example, the protein can be eluted from the substrate under appropriate conditions. In some cases, the compositions provided herein can provide for a reversibly immobilized protein that can be eluted from the substrate without the formation, without substantial formation, or wherein less than about 50%, 40%, 30%, 20%, 10%, 5%, 2%, or 1% of the eluted protein is aggregated.

In some embodiments, the substrate is not a lateral flow assay substrate. For example, in some cases, the substrate does not contain an antibody that is never eluted from the substrate during use. In some cases, the substrate does not contain an antibody that is irreversibly immobilized to the substrate or is not elutable from the substrate. In some cases, the substrate does not host a binding reaction or enzymatic reaction.

C. Protein Aggregation Modifying Agents

As described herein, protein aggregation modifying agents can be utilized to reduce or eliminate aggregation or denaturation of proteins stored on, or delivered from, a substrate. In some cases, protein aggregation modifying agents that act to displace proteins from the air-water interface and thereby protect them from denaturation and aggregation are particularly effective in reducing the aggregation of proteins immobilized on a porous substrate. In other cases, the protein aggregation modifying agent directly affects the stability of the protein by binding to the protein and/or stabilizing the protein. In other cases, the protein aggregation modifying agent acts to shift the equilibrium away from the denatured or unfolded state and thus reduce aggregation. For example, in some cases, the interaction between the protein aggregation modifying agent and the protein is thermodynamically disfavored due to strong repulsion between the amide backbone of the protein and the protein aggregation modifying agent. Thus, unfolding of the protein in the presence of the protein aggregation modifying agent is disfavored because unfolding exposes more protein amide backbone surface to the protein aggregation modifying agent.

Protein aggregation modifying agents can include one or more of a cyclodextrin, a non-ionic surfactant, an ionic surfactant, a zwitterionic surfactant, a non-detergent sulfobetaine, a simple sugar, a polysaccharide, a polyol, an organic solvent, an aggregation modifying protein, a disordered peptide sequence, an amino acid, an oxido-reduction agent, a lyoprotectant, a cryoprotectant, and a chaotropic agent.

Cyclodextrins include, but are not limited to, α-cyclodextrin, β-cyclodextrin, γ-cyclodextrin, (2,3,6-tri-O-methyl)-β-cyclodextrin, (2,3,6-tri-O-methyl)-β-cyclodextrin, (2-hydroxy)propyl-β-cyclodextrin, (2-hydroxy)propyl-γ-cyclodextrin, random methyl-β-cyclodextrin, random methyl-γ-cyclodextrin, carboxymethyl-β-cyclodextrin, carboxymethyl-γ-cyclodextrin, 6-monodeoxy-6-monoamino-β-cyclodextrin, sulfobutyl-β-cyclodextrin, 6-amino-6-deoxy-β-cyclodextrin, acetyl β-cyclodextrin, succinyl α-cyclodextrin, succinyl β-cyclodextrin, succinyl γ-cyclodextrin, (2,3,6-tri-O-benzoyl)-β-cyclodextrin, succinyl-(2-hydroxypropyl)-β-cyclodextrin, and succinyl-(2-hydroxypropyl)-γ-cyclodextrin. Cyclodextrins can also include cyclodextrin polymers containing one or more of the foregoing cyclodextrin molecules. Additional cyclodextrins are known in the art, and include, e.g. those described on the world wide web at cyclodextrin.com. Exemplary concentrations of cyclodextrins include, but are not limited to about 1 mM, 2 mM, 2.5 mM, 5 mM, 7.5 mM, 10 mM, 15 mM, 20 mM, 25 mM, 50 mM, 75 mM, or 100 mM.

Non-ionic surfactants include polyethylen-sorbitan-fatty acid esters, polyethylene-polypropylene glycols and polyoxyethylene-stearates. Polyethylen-sorbitan-fatty acid esters include polyethylen(20)-sorbitan-esters (Tween20™) and polyoxyethylene(20)-sorbitanmonooleate (Tween 80™). Polyethylene-polypropylene glycols include polyoxypropylene-polyoxyethylene block co-polymers such as those sold under the names Pluronic® or Poloxamer™. Polyoxyethylene-stearates include those sold under the trademark Myrj™. Polyoxyethylene monolauryl ethers include those sold under the trademark Brij™, e.g., Brij-35. Exemplary concentrations of non-ionic surfactants include, but are not limited to about 0.01%, 0.02%, 0.05%, 0.1%, 0.2%, 0.5%, 0.75%, 1%, 2%, 2.5%, 5%, 7.5%, and about 10% w/w, w/v, or v/v.

Ionic surfactants include anionic surfactants and cationic surfactants. Anionic surfactants useful in the present invention include, but are not limited to soaps including alkali soaps, such as sodium, potassium and ammonium salts of aliphatic carboxylic acids, usually fatty acids, such as sodium stearate. Additional anionic surfactants include organic amine soaps such as organic amine salts of aliphatic carboxylic acids, usually fatty acids, such as triethanolamine stearate. Cationic surfactants useful in the present invention include, but are not limited to, amine salts such as octadecyl ammonium chloride and quarternary ammonium compounds such as benzalkonium chloride. Ionic surfactants further include the sodium, potassium and ammonium salts of alkyl sulfates, such as sodium dodecyl sulfate and sodium octyl sulfate. Exemplary concentrations of ionic surfactants include, but are not limited to about 0.01%, 0.02%, 0.05%, 0.1%, 0.2%, 0.5%, 0.75%, 1%, 2%, 2.5%, 5%, 7.5%, and about 10% w/w, w/v, or v/v.

Zwitterionic surfactants have both cationic and anionic centers attached to the same molecule. The cationic part is, e.g., based on primary, secondary, or tertiary amines or quaternary ammonium cations. The anionic part can include sulfonates, as in CHAPS (3-[(3-Cholamidopropyl)dimethylammonio]-1-propanesulfonate). Other anionic groups are sultaines illustrated by cocamidopropyl hydroxysultaine and betaines, e.g., cocamidoethyl betaine, cocamidopropyl betaine, or lauramidopropyl betaine. Exemplary concentrations of zwitterionic surfactants include, but are not limited to about 0.01%, 0.02%, 0.05%, 0.1%, 0.2%, 0.5%, 0.75%, 1%, 2%, 2.5%, 5%, 7.5%, and about 10% w/w, w/v, or v/v.

Non detergent sulfobetaines (NDSBs) have a sulfobetaine hydrophilic group and a short hydrophobic group that cannot aggregate to form micelles, therefore NDSBs are not considered detergents. NDSBs include, but are not limited to NDSB 256, NDSB 221, NDSB 211, NDSB 201, NDSB 195, 3-(4-tert-Butyl-1-pyridinio)-1-propanesulfonate, 3-(1-pyridinio)-1-propanesulfonate, 3-(Benzyldimethylammonio) propanesulfonate, and Dimethylethylammoniumpropane sulfonate. Exemplary concentrations of NDSBs include, but are not limited to about 0.01%, 0.02%, 0.05%, 0.1%, 0.2%, 0.5%, 0.75%, 1%, 2%, 2.5%, 5%, 7.5%, and about 10% w/w, w/v, or v/v.

Polyols are compounds with multiple hydroxyl functional groups. In some cases, polyols can modify the aggregation or denaturation behavior of a protein by a variety of mechanisms. For example, in some cases, the polyol can shift the equilibrium to the folded state by presenting a thermodynamically disfavored interaction with the protein backbone. Alternatively, in some cases, the polyol can bind to and stabilize the folded state of the protein.

Polyols can include simple sugars such as sucrose, mannitol, sorbitol, inositol, xylitol, erythritol, glucose, galactose, raffinose, and trehalose. Polyols can also include polysaccharides such as dextran, starch, hydroxyethyl starch, and polymers containing the simple sugars described herein. Polyols can also include glycerol, ethylene glycol, polyethylene glycol, pentaerythritol propoxylate, and pentaerythritol propoxylate, and combinations thereof.

Organic solvents include, but are not limited to, those organic solvent that are known to inhibit denaturation, unfolding, or aggregation of one or more proteins. A variety of suitable organic solvents are known in the art. For example, organic solvents can include ethanol, butanol, propanol, phenol, dimethyl formamide, 2-methyl-2,4-pentanediol, 2,3-butanediol, 1,2-propanediol, 1,6-hexanediol, and dimethyl sulfoxide.

Aggregation modifying proteins include proteins known in the art to inhibit denaturation, unfolding, or aggregation of one or more proteins. Aggregation modifying proteins include, but are not limited to, albumins. Albumins are proteins that are water-soluble, are moderately soluble in concentrated salt solutions, and experience heat denaturation. Albumins include serum albumins (e.g., bovine, horse, or human serum albumin) and egg albumin (e.g., hen egg-white albumin). Aggregation modifying proteins also include casein, gelatin, ubiquitin, lysozyme, and late embryogenesis abundant (LEA) proteins. LEA proteins include LEA I, LEA II, LEA III, LEA IV, LEA V, and atypical LEA proteins. LEA proteins are known in the art and described, e.g., in Goyal K., et al., Biochemical Journal 288(pt. 1), 151-57, (2005).

Protein aggregation modifying agents include amino acids. In some cases, the amino acids can serve an oxido-reduction function to maintain an appropriate oxidative potential for the protein immobilized on the substrate. Suitable oxido-reducitve amino acids include cysteine and cystine. Other amino acids serve to reduce denaturation or aggregation through a non-oxido-reductive method. For example, arginine, glycine, proline, and taurine have been shown to reduce protein aggregation.

Other oxido-reduction agents can be employed to reduce protein aggregation. Oxido-reductants other than cysteine and cystine, can be used to optimize the reduction potential in the substrate onto which the protein is immobilized. Additional oxido-reductants include mercaptoethanol, dithiothreitol, dithioerythritol, tris(2-carboxyethyl)phosphine, glutathione, glutathione disulfide, and oxidized derivatives thereof, as well as $Cu^{2+}$.

Protein aggregation modifying agents can also include lyoprotectants, cryoprotectants, or chaotropic agents. In some cases, the protein aggregation modifying agent is a chaotrope such as urea, thiourea, guanidinium, cyanate, thiocyanate, trimethylammonium, tetramethylammonium, cesium, rubidium, nitrate, acetate, iodide, bromide, trichloroacetate, or perchlorate. Under certain conditions, such as at low concentrations, chaotropes can reduce protein aggregation. Other protein aggregation modifying agents include trimethylamine N-oxide.

Protein aggregation modifying agents can further include salts. Salts include, but not limited to, the sodium, potassium, magnesium, and calcium salts of chloride, sulfate, and phosphate. Protein aggregation modifying agents can further include buffering agents. Exemplary buffering agents include, but are not limited to, tris (hydroxymethyl) amino methene (TRIS), TAPSO, MES, HEPES, PIPES, CAPS, CAPSO, MOPS, MOPSO, and sodium or potassium phosphate, carbonate, bicarbonate, citrate, acetate, or borate buffers.

The protein aggregation modifying agents can be provided in any suitable concentration. In some cases, the protein is provided as an aqueous solution containing protein and protein aggregation modifying agents. In such cases, the solution can be contacted with a substrate and, optionally, dried. Exemplary concentrations of protein aggregation modifying agents in the aqueous protein solution include, but are not limited to, about 0.001%, 0.005%, 0.01%, 0.05%, 0.1%, 0.5%, 1%, 2%, 4%, 5%, 10%, 20%, or about 25% or more w/v of the solution. Further exemplary concentrations include, but are not limited to, about 1 µM, 5 µM, 10 µM, 25 µM, 50 µM, 75 µM, 100 µM, 150 µM, 200 µM, 300 µM, 500 µM, 750 µM, 1 mM, 5 mM, 10 mM, 25 mM, 50 mM, 100 mM, 150 mM, 200 mM, 300 mM, 500 mM, and 1M.

In some cases, the protein aggregation modifying agents are provided on the substrate. Exemplary compositions containing a protein aggregation modifying agent and a substrate include, substrates that contain about 0.001%, 0.005%, 0.01%, 0.05%, 0.1%, 0.5%, 1%, 2%, 3%, 4%, 5%, or about 10%, 20%, or about 25% by weight of protein aggregation modifying agents.

Protein aggregation modifying agents can be provided in any suitable combination. For example, in some cases, 1, 2, 3, 4, 5, 6, 7, 8, 9, 10 or more of the foregoing protein aggregation modifying agents can be utilized to reduce aggregation of a protein immobilized on a substrate. In some cases, prior to contacting the substrate with the protein solution, the substrate contains a protein aggregation modifying agent, and the protein solution contains a different protein aggregation modifying agent. In other cases, the substrate contains a protein aggregation modifying agent and the protein solution contain the same protein aggregation modifying agent. In some cases, prior to contacting the substrate with the protein solution, the substrate contains a protein aggregation modifying agent, and the protein solution does not contain a protein aggregation modifying agent. In some cases, prior to contacting the substrate with the protein solution, the protein solution contains a protein aggregation modifying agent and the substrate does not.

D. Eluent

In some embodiments, eluents (e.g., elution buffers) can be used for obtaining a protein that has been stored (e.g., reversibly immobilized) on a substrate. The eluents described herein are generally water or buffered aqueous solutions that are capable of wetting the substrate and solubilizing the reversibly immobilized proteins. Virtually any pH buffering composition that is soluble in water and generally compatible with proteins can be utilized. Exemplary buffering agents include, but are not limited to, tris (hydroxymethyl) amino methene (TRIS), TAPSO, MES, HEPES, PIPES, CAPS, CAPSO, MOPS, MOPSO, and sodium or potassium phosphate, carbonate, bicarbonate, citrate, acetate, or borate buffers.

The eluent can also contain various compositions that aid in protein solubilization or stabilization. For example, the eluent can contain any of the foregoing protein aggregation modifying agents. Alternatively, the eluent (e.g., water) can acquire a protein solubilization or stabilization function by dissolving buffers and/or protein aggregation modifying agents present on the substrate. In any case, the concentration of one or more protein aggregation modifying agents present in an eluent can be the same or different from the concentration utilized during the reversible immobilization process.

The eluent can be a transfer buffer for transferring the reversibly immobilized protein to a second substrate or to a membrane. One of skill in the art will understand that there are a wide variety of suitable transfer buffer compositions, such as a western blot transfer buffer. Western blot transfer buffer commonly contains one or more of tris-(hydroxymethyl)-aminomethane (Tris), N-cyclohexyl-3-aminopropanesulfonic acid (CAPS), glycine, methanol, ethanol, and propanol. In some cases, western blot transfer buffer can also contain a low concentration of denaturing agent such as a detergent (e.g., sodium dodecyl sulfate) or a chaotrope (e.g., urea). In cases where the transfer will occur in response to an applied voltage potential, the transfer buffer can be buffered at a pH that is above the isoelectric point of the one or more reversibly immobilized proteins so that the transfer occurs toward the positive electrode. Alternatively, the transfer buffer can be buffered at a pH that is below the isoelectric point of the one or more reversibly immobilized proteins so that the transfer occurs toward the negative electrode.

IV. Methods

Described herein are methods of storing or delivering proteins that are immobilized (e.g., reversibly immobilized) on a substrate. In general, these methods rely on the inventors' surprising discovery that the presence of certain compositions, referred to herein as protein aggregation modifying agents, reduce or eliminate aggregation of the protein during the process of reversibly immobilizing the protein onto the substrate, the process of storing the reversibly immobilized protein on the substrate, the process of wetting a substrate containing a protein, or the process of eluting the protein from the substrate.

A. Storage

In some embodiments, one or more proteins are stored on a substrate by reversibly immobilizing the protein onto the substrate. In some embodiments, the method includes:

providing a porous substrate and a protein aggregation modifying agent;

contacting the porous substrate in the presence of the protein aggregation modifying agent with a solution containing a protein; and reversibly immobilizing the protein on the porous substrate, thereby storing the reversibly immobilized protein on the porous substrate.

The method includes providing or obtaining a suitable substrate. Suitable substrates are described above and include various porous substrates. In some cases, the substrate is provided dry. In other cases, the substrate is provided wet. For example, the substrate can be wetted with a solution containing a protein aggregation modifying agent. In other cases, the substrate is wetted before contact with the protein with a solution containing a protein aggregation modifying agent and the dried before contact with the protein. In some cases, the providing is performed by ordering or obtaining a substrate suitable for the storage or delivery from another party.

The method further includes contacting the porous substrate with a solution containing the protein. As explained above, the protein can be virtually any protein or combination of proteins. For example, the protein can be an antibody, or 2, 3, 4, 5, or more antibodies. In some cases, the substrate has only one antibody immobilized, only one antibody reversibly immobilized, only two antibodies immobilized, or only two antibodies reversibly immobilized on the substrate.

The contacting can be performed in any manner desired. Such contacting steps can include spraying a protein solution onto one or two sides, or a portion thereof, of the substrate, dipping at least a portion of the substrate into the protein solution, brushing the protein solution onto at least a portion of the substrate, coating at least a portion of the substrate with the protein solution, pouring or pipetting. In some cases, the spraying, dipping, brushing, coating, pouring, or pipetting is performed multiple times for each protein to be reversibly immobilized onto the substrate. In other cases, a protein solution containing all the proteins to be reversibly immobilized onto the substrate is utilized. In still other cases, multiple contacting steps are performed with proteins solutions of the same or differing compositions.

In some cases, the contacting is performed manually. For example, the substrate can be dipped into a suitable protein solution manually, or the solution can be pipetted or sprayed onto the substrate manually. In other cases, the contacting is performed using an instrument, or an automated or robotic platform. For example, a pipetting instrument, a spraying instrument (e.g., a modified ink-jet apparatus), or other automated or robotic platform.

In some cases, the contacting is performed such that one or more proteins are reversibly immobilized in a spatially addressable fashion. For example, the one or more proteins may be sprayed from an ink-jet modified to spray solutions containing a biomolecule, applied via a precision pipetting instrument, and the contacting can be performed manually such that the protein is reversibly immobilized at a specified location, which location can be determined or tracked after the reversible immobilization. In some cases, the substrate can be contacted in a reversible immobilization region. For example, the reversible immobilization region can be at least partially delineated or surrounded by a mask region or an annotation mark. In some cases, a first protein is reversibly immobilized in one region delineated by a first mask region or annotation mark, and a second protein is reversibly immobilized in a second region delineated by a second mark. The process can be performed, if desired, for 2, 3, 4, 5, 6, 7, 8, 9, 10 or more proteins, each reversibly immobilized at a specified location.

In some cases, the protein is stored across a large region of the substrate surface. For example, the reversibly immobilized protein can be reversibly immobilized across at least 30%, 40%, 50%, 60%, 70%, 80%, 90%, 95%, 99%, all, or substantially all of at least one surface of the substrate, or at least 30%, 40%, 50%, 60%, 70%, 80%, 90%, 95%, 99%, all, or substantially all of a reversible immobilization region.

The substrate can be contacted with the protein in the presence of one or more protein aggregation modifying agents. For example, the substrate can be contacted first with a solution containing one or more protein aggregation modifying agents, optionally dried, and then contacted with the protein. Alternatively, or additionally, the protein solution can contain one or more protein aggregation modifying agents. As yet another alternative, one or more protein aggregation modifying agents can also be applied after the protein is contacted with the substrate. Thus, the protein can be contacted with the substrate before a protein aggregation modifying agent is applied, simultaneously with the application of a protein aggregation modifying agent, after application of a protein aggregation modifying agent, or a combination thereof.

The protein can then be reversibly immobilized onto the substrate. Reversible immobilization can occur via a specific binding reaction (e.g., to a ligand present on the substrate), non-specific adsorption, drying of the protein solution and substrate, or via the formation of a reversible (e.g., cleavable) covalent bond between the substrate and the protein. In any case, the protein can be protected from denaturation or aggregation during the reversible immobilization by the presence of one or more protein aggregation modifying agents.

In some cases, the protein is reversibly immobilized on the substrate by drying the substrate. In general, drying can be performed by allowing or causing the volatile solvents (e.g., water, ethanol, etc.) in which the protein is solubilized to evaporate. Such evaporation can be performed at room temperature and pressure (e.g., about 297 K and 1 atmosphere of pressure). Alternatively, the evaporation can be performed at higher temperature, lower pressure, or any suitable combination thereof. For example, the drying may be performed under lyophilization conditions such as under reduced temperature and pressure. In some cases, the drying may be performed at a temperature and pressure at which water sublimes from solid to gas without transitioning through a liquid phase. Drying can therefore include air drying, vacuum drying, drying in an oven at an elevated temperature (e.g., 27, 30, 35, 50, 55, 60, 65, 70, 80, or 90° C. or more), and lyopholization.

In some cases, e.g., where the reversible immobilization does not include a drying step, the substrate containing the reversibly immobilized protein can be stored wet. For example, the substrate can be placed in a container such that the protein is on the substrate and the substrate is wet. In some cases, the amount of liquid in the container is at or below the liquid absorbance capacity of the substrate.

The storage liquid can be the same as the solution in which the protein was contacted with the substrate, or can be a different solution. For example, the substrate can be contacted with a solution containing a protein, dried, and then contacted with a storage solution. The storage solution can be the same as the eluent, or can be a different solution. For example, the substrate can be contacted with a solution containing a protein, dried, contacted with an amount of eluent at or below the absorbance capacity of the substrate, optionally stored, and then contacted with an additional amount of eluent to elute the reversibly immobilized protein. In some cases, the storage solution contains one or more protein aggregation modifying agents.

The substrate containing the reversibly immobilized protein can be stored at any suitable temperature as known in the art for storage of proteins. For example, the substrate can be stored at room temperature, or at 10, 5, 4, 3, 2, 1, 0, −5, −10, or −20° C., or lower. In some cases, the substrate can be stored at room temperature if it is dry or substantially dry and stored at lower than room temperature (e.g., 10, 5, 4, 3, 2, 1, 0, −5, −10, or −20° C., or lower) if it is wet.

The protein reversibly immobilized on the substrate can be stored for any suitable length of time. Alternatively, the protein can be reversibly immobilized on the substrate and then used immediately, or almost immediately (e.g., within 1, 2, 3, 4, 5, 6, 10, 15, 30, 60 minutes, or within 2, 3, 4, 5, 6, 7, 8, 10, 12, 14, 18, 24, or 48 hours). For example, the protein may be contacted with the substrate and then placed into contact with a second substrate or a membrane to transfer the protein to the second substrate or membrane. As another example, the protein can be contacted with the substrate and then placed into a transfer apparatus.

Suitable storage times include 1, 2, 3, 4, 5, 6, 7, 8, 9, 10, 12, 14, 21, 30, 60, or 90 days or more. Suitable storage times further include 3, 4, 5, 6, 7, 8, 9, 10, 11, or 12 months or more. One of skill in the art will recognize that storage times will vary based on the storage conditions, and the reason for the storage. For example, in some cases, the reversibly immobilized protein may be stored longer at colder temperatures (e.g., 10, 5, 4, 3, 2, 1, 0, −5, −10, or −20° C., or lower).

As another example, in some cases, the immobilization or storage may be performed by an entity that sells the protein or provides the protein to others. Thus, the protein may be stored until an order or request is received and the protein has been delivered. In such an example, the storage time may include the time for transit (e.g., postal service, delivery company, or courier) and receipt of the reversibly immobilized protein. Storage time may also include storage by a manufacturer, a consumer, a distributor, or a retailer.

B. Delivery

Described herein, are methods for delivering a protein from a substrate (e.g., a porous substrate). In some embodiments, the steps of the method are:
providing a porous substrate containing a reversibly immobilized protein and a protein aggregation modifying agent; and
eluting the reversibly immobilized protein from the porous substrate with an eluent, thereby delivering the protein.

In some cases, at least 30%, 40%, 50%, 60%, 70%, 80%, 90%, 95%, 99%, all, or substantially all of the reversibly immobilized protein is eluted from the porous substrate. In some cases, at least 30%, 40%, 50%, 60%, 70%, 80%, 90%, 95%, 99%, all, or substantially all of the eluted protein is non denatured or non-aggregated.

Generally, the delivering involves contacting the substrate with an eluent, solubilizing the reversibly immobilized protein, and collecting the eluent. The contacting can be performed by dipping, coating, pipetting, pouring, spraying, or contacting the substrate with a second substrate, a membrane, or a filter paper that contains eluent. In some cases, the delivery includes delivering the protein into a solution. In some cases, the delivery includes delivering the protein onto a second substrate, a gel, or a membrane (e.g., a western blot).

In some embodiments, the reversibly immobilized protein is contacted with an eluent and the eluent, with at least a portion of the protein, is collected in a container. For example, the substrate can be contacted with an eluent, the protein solubilized, and then the eluent can be separated from the substrate. For example, the substrate and eluent can be centrifuged or the eluent can be recovered by filtration, (e.g., vacuum filtration). Alternatively, the substrate can be contacted with an eluent and subjected to capillary action, vacuum, pressure, or the application of an electromagnetic force to cause the eluent, the protein, or both the eluent and the protein to elute from the substrate.

The electromagnetic force can include an applied voltage or a magnetic field. In some cases, the eluent is at a pH that is above the isoelectric point of the protein and the electromagnetic force is applied to drive protein toward a positive electrode. In other cases, the eluent is at a pH that is below the isoelectric point of the protein and the electromagnetic force is applied to drive the protein toward a negative electrode. In some cases, the protein is bound to a charged molecule or a plurality of charged molecules and the electromagnetic force is applied to drive the protein toward an electrode of the opposite charge. In some cases, the protein is labeled with a magnetic bead or particle, and a magnetic field is utilized to elute the protein. Alternatively, the magnetic bead or particle may be located on a ligand that has affinity for the protein.

In some embodiments, the reversibly immobilized protein is transferred to a second substrate, a gel (e.g., an acrylamide or agarose gel), or a membrane. For example, the substrate can be contacted with an eluent, and the protein allowed to diffuse onto a second substrate, a gel, or a membrane. Alternatively, the substrate can be contacted with an eluent and subjected to capillary action, vacuum, pressure, or the application of an electromagnetic force to cause the eluent, the protein, or both the eluent and the protein to migrate toward the second substrate, gel, or membrane.

In some cases, the membrane, the gel, or the second substrate includes one or more proteins immobilized thereon. The immobilized protein(s) are generally irreversibly immobilized, or substantially irreversibly immobilized. For example, in some cases, at least 50%, 60%, 70%, 80%, 90%, 95%, 99%, all, or substantially all of the immobilized protein(s) on the second substrate, the gel, or the membrane are not eluted by contact with the eluents described herein.

In some embodiments, the presence of the transferred protein can then be detected in or on the second substrate, the gel, or the membrane. For example, the presence or absence of a detectable label directly or indirectly linked to the transferred protein can be determined. Alternatively, a binding reagent (e.g., a secondary antibody such as a labeled secondary antibody) can be used to detect the presence or absence of the transferred protein. In some cases, the transfer of the reversibly immobilized protein from a first substrate to a second substrate, or from the substrate to a gel or a membrane can lead to binding of the reversibly immobilized protein to a protein that is immobilized on the second substrate or the membrane, or immobilized in the gel. In such cases, the detecting of the transferred protein thereby detects the presence of the immobilized protein on the second substrate or the membrane, or in the gel. In some cases, the reversibly immobilized protein can be one or more antibodies for detection of one or more epitopes present on the second substrate or membrane, or present in the gel. In some cases, such detection methods constitute a western blot.

V. Articles of Manufacture and Kits

Described herein are articles of manufacture that include one or more protein(s), one or more protein aggregation modifying agent(s), and a substrate. The protein can be any labeled or unlabeled protein as described above. The protein aggregation modifying agent can be any cyclodextrin, non-ionic surfactant, ionic surfactant, zwitterionic surfactant, non-detergent sulfobetaine, simple sugar, polysaccharide, polyol, organic solvent, aggregation modifying protein, disordered peptide sequence, amino acid, oxido-reduction agent, lyoprotectant, cryoprotectant, or chaotropic agent as described above. The substrate can be any of the substrates as described above. In some cases, the substrate is a porous substrate.

Also described herein are kits that include one or more (e.g., 2, 3, 4, 5, 6, 7, 8, 9, 10, 11, 12, 13, 14, 15, 20, 25, 30, 40, 50, or more) of the foregoing substrates, or one or more (e.g., 2, 3, 4, 5, 6, 7, 8, 9, 10, 11, 12, 13, 14, 15, 20, 25, 30, 40, 50, or more) of the foregoing articles of manufacture. In some cases, the kits can further include instructions for reversibly immobilizing a protein, instructions for use of one or more components of the kit to detect a protein, or instructions for eluting a reversibly immobilized protein from a component of the kit. In some cases, the kit can include elution buffer, one or more components of an elution buffer, or an elution buffer concentrate (e.g., 10× elution buffer). In some cases, the kit can include one or more protein aggregation modifying agents.

EXAMPLES

The following examples are offered to illustrate, but not to limit the claimed invention.

Example 1

Transfer to a Membrane or a Gel for Detection of Immobilized Proteins

Figure 1:
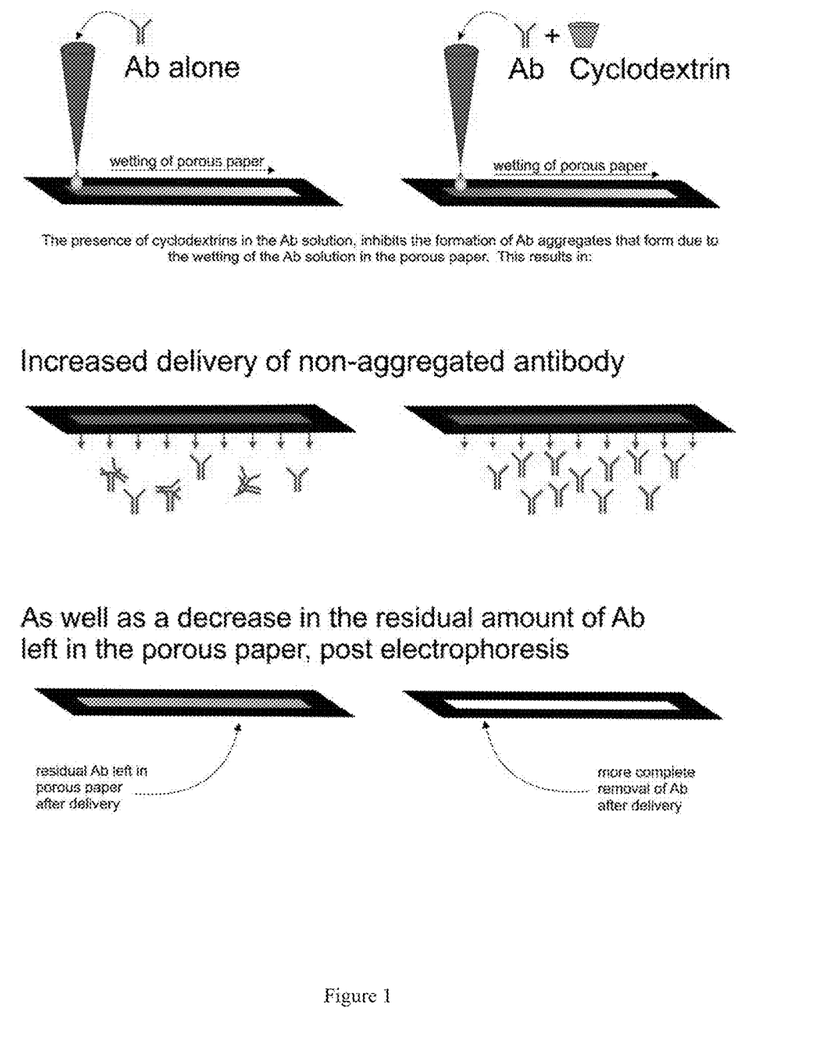
FIG. 1: depicts the use of the protein aggregation modifying agent cyclodextrin to inhibit the formation of antibody aggregates formed by wetting a porous substrate with a solution containing the antibody. As illustrated, this results in an increased delivery of non-aggregated antibody and more complete removal of antibody from the substrate.
Figure 2:
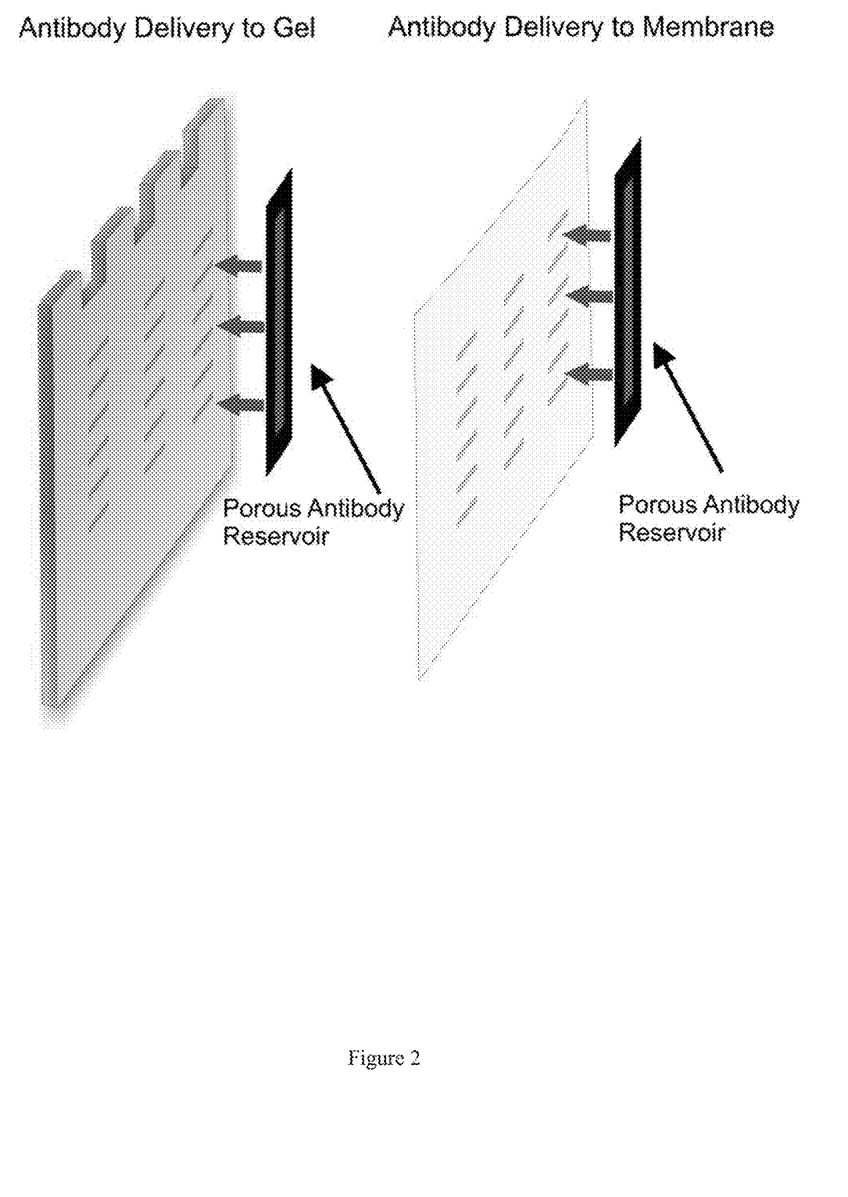
FIG. 2: depicts delivery of antibody from a porous substrate to a gel or a membrane. As illustrated by gray lines, the gel or the membrane can contain immobilized target proteins.
Figure 3:
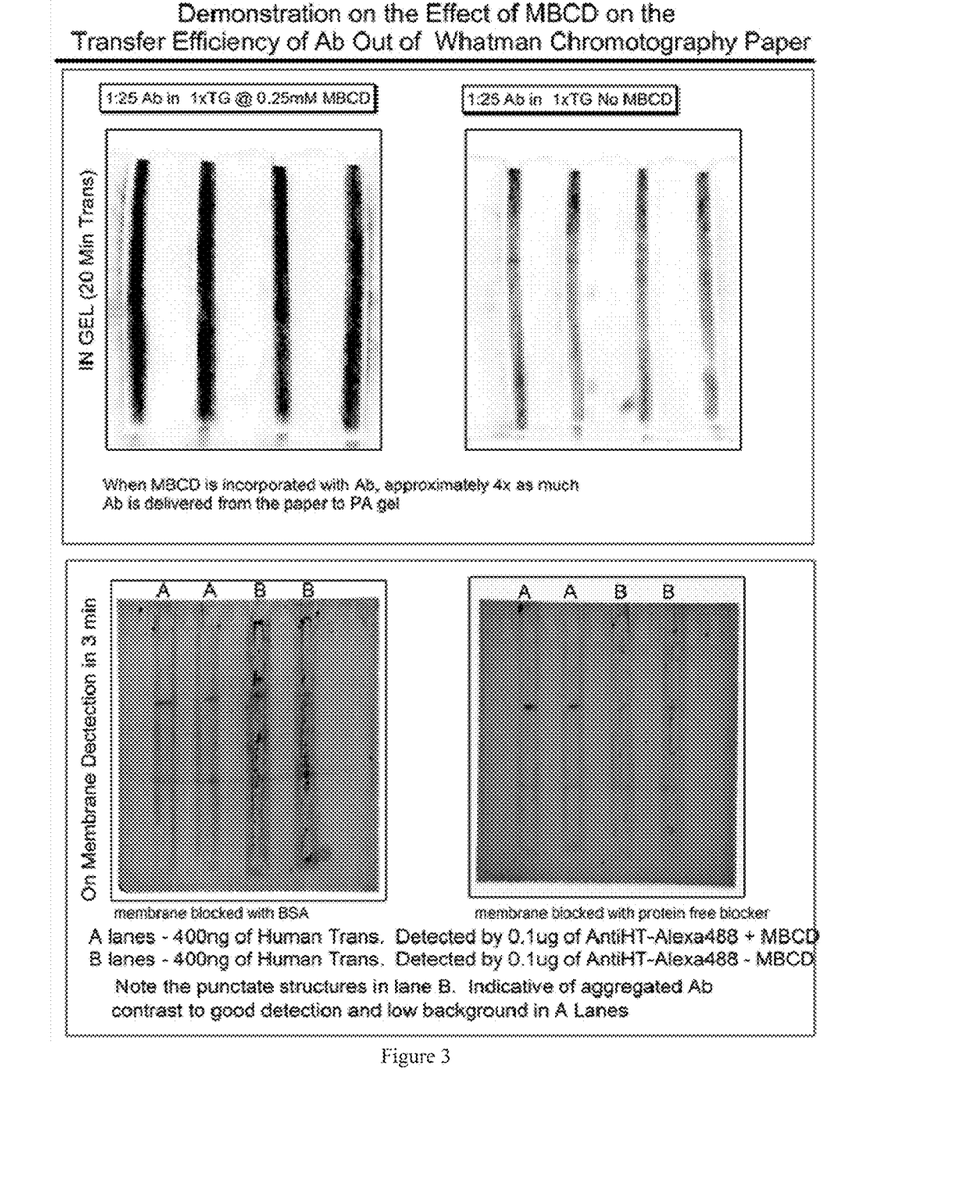
FIG. 3: demonstrates the effect of methyl-beta-cyclodextrin (MBCD) on the transfer efficiency of antibody out of Whatman® chromatography paper.

Using a pipette, 20 µL of antibody (Ab) solution is delivered to one end of a strip of chromatography paper. The antibody solution is prepared in 1× Tris-Gly buffer (Bio-Rad) in the presence or absence of 0.25 mM methyl-B-cyclodextrin (MBCD). This is shown in the top of FIG. 1. During wetting of the porous paper, the MBCD protects the Ab from forming Ab aggregates. These Ab soaked paper strips are then overlaid on top of either polyacrylamide gels (with immobilized antigens) or nitrocellulose membranes with blotted antigens (shown in FIG. 2). These are then sandwiched between two transfer pads (Bio-Rad Transblot-Turbo pads), soaked in 1×Tris Gly buffer. Antibody is then electrophoretically transferred from the porous paper substrates to the gel or membrane surface using the Transblot-Turbo. In the case of the gel, the Ab strips are loaded at a concentration of 1:25, in the case of the nitrocellulose membrane, the Ab strips are loaded at a concentration of 1:200. The result of transfer to a gel is demonstrated in the top of FIG. 3 (transfer condition: 0.3 amp for 20 minutes). This image shows that approximately 4× as much antibody is delivered from the paper strip that contained the MBCD, indicating that in the absence of MBCD, Ab is increasingly retained in the paper strip, post electrophoresis. This is graphically demonstrated in the bottom of FIG. 1. The results of transfer to the membrane are demonstrated in the bottom of FIG. 3 (transfer condition: 0.3 amp for 3 minutes). This image shows that in the absence of Ab, a significant amount of the Ab is delivered from the paper as an aggregate. This is demonstrated in the "B" lanes of the membranes which show increased "splotchy" background, compared to the "A" lanes which show clean background after transfer indicating a transfer of monomeric Ab. This is graphically demonstrated in the middle of FIG. 1. The two membranes in the bottom of FIG. 3 are blocked with either 3% BSA (Left), or Pierce Protein Free Blocker (Right).

Example 2

Spatially Controlled Antibody Delivery to a Membrane

Figure 4:
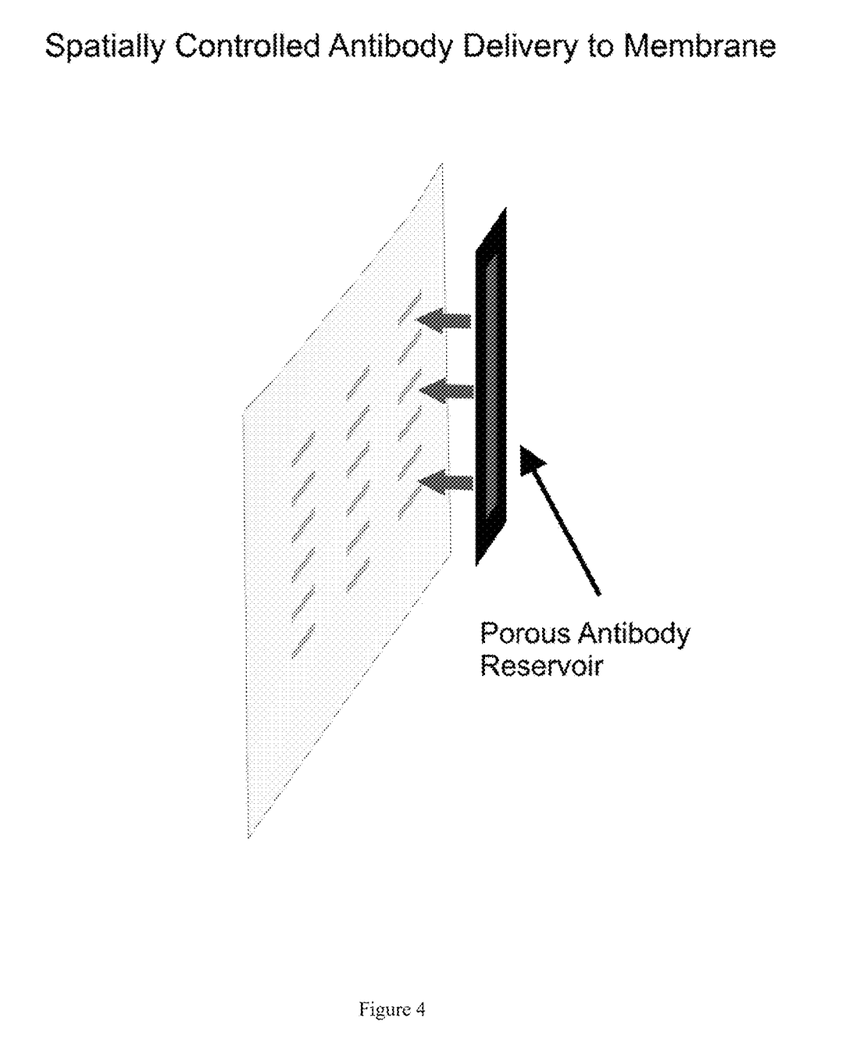
FIG. 4: depicts one method of spatially controlled antibody delivery to a membrane.

A membrane is provided that contains lanes or columns of immobilized proteins. A porous substrate containing an antibody is contacted with one of the lanes or columns to effect transfer of the antibody to the membrane, as shown in FIG. 4.

Example 3

Spatially Controlled Detection of Target Proteins

Figure 5:
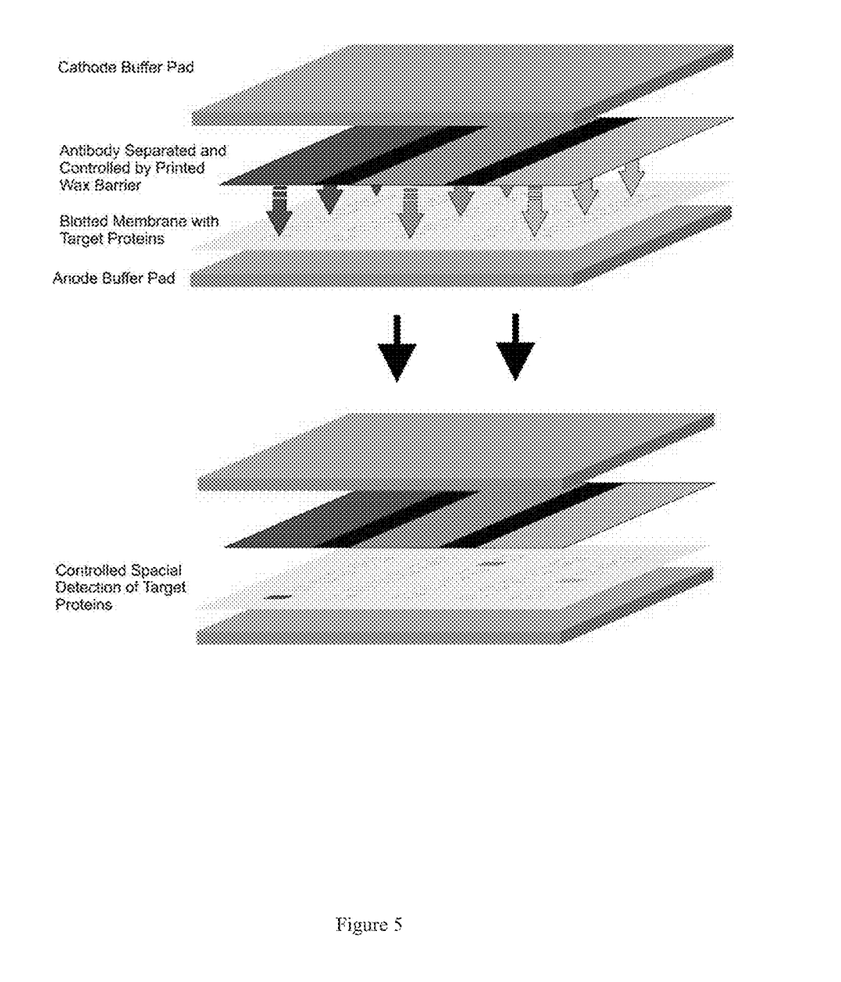
FIG. 5: depicts the use of wax barriers to deliver multiple antibodies to a membrane in a spatially controlled manner.

A membrane is provided that contains immobilized proteins. A porous substrate containing a first antibody localized to a first region, a second antibody localized to a second region, and a third antibody localized to a third region. The first, second, and third regions are separated by a wax barrier. The substrate is contacted with the membrane, and the substrate:membrane sandwich is placed between a cathode buffer pad and an anode buffer pad. A voltage is applied via the cathode and anode to effect transfer of the antibody to the membrane. The binding of the first, second, or third antibody in the regions in contact with the spatially controlled first, second, and third regions of the substrate leads to spatially controlled detection of target proteins as shown in FIG. 5.

All patents, patent applications, and other publications, including GenBank Accession Numbers, cited in this application are incorporated by reference in the entirety for all purposes.

What is claimed is:

1. A method of delivering a protein, the method comprising:
   providing a porous substrate comprising a reversibly immobilized protein and a protein aggregation modifying agent, wherein the protein aggregation modifying agent is a cyclodextrin; and
   eluting the reversibly immobilized protein from the porous substrate with an eluent comprising a cyclodextrin,
   thereby delivering the protein.

2. The method of claim 1, wherein the eluent comprises a buffered solution at a pH above the isoelectric point of the reversibly immobilized protein.

3. The method of claim 1, wherein the eluent comprises a western blot transfer buffer comprising tris(hydroxymethyl)aminomethane (Tris), N-cyclohexyl-3-aminopropanesulfonic acid (CAPS), glycine, methanol, ethanol, or propanol.

4. The method of claim 1, wherein the eluent comprises a western blot transfer buffer comprising two or more compounds selected from the group consisting of tris-(hydroxymethyl)-aminomethane (Tris), N-cyclohexyl-3-aminopropanesulfonic acid (CAPS), glycine, methanol, ethanol, and propanol.

5. The method of claim 1, wherein the eluting comprises subjecting the substrate to diffusion, capillary action, vacuum, pressure, or electrophoresis, or contacting the porous substrate with a magnetic particle that has an affinity for the reversibly immobilized protein.

6. The method of claim 1, wherein the method comprises eluting at least 50% of the reversibly immobilized protein from the porous substrate with an eluent.

7. The method of claim 1, wherein the eluting comprises eluting a portion of the protein onto a membrane.

8. The method of claim 7, wherein the membrane has an immobilized protein on its surface.

9. The method of claim 8, wherein non-specific binding sites on the membrane are blocked.

10. The method of claim 7, wherein the method further comprises washing non-specifically bound and unbound eluted protein from the membrane.

11. The method of claim 7, wherein the method further comprises detecting the presence of the eluted protein on the membrane.

12. The method of claim 11, wherein the method further comprises
binding the protein eluted from the substrate to the immobilized protein on the membrane surface; and
detecting the presence of the eluted protein on the membrane,
thereby detecting the presence of the immobilized protein on the membrane surface.

13. The method of claim 1, wherein 1, 2, 3, 4 or more different proteins are reversibly immobilized on the porous substrate.

14. The method of claim 1, wherein the porous substrate comprises a composition selected from the group consisting of whatman paper, a cellulose filter, a glass microfiber filter, nitrocellulose, polyvinylidene difluoride, a sintered glass, a sintered polymer, a sintered metal, a spunbound polyester, rayon, nylon, a porous polymer monolith, a porous polymer bead, a capillary wicking bed, natural or synthetic sponge, and fiberglass.

15. The method of claim 1, wherein the porous substrate comprises a mask region and a reversible immobilization region, wherein reversibly immobilized protein is immobilized on the reversible immobilization region.

16. The method of claim 1, wherein the protein is reversibly immobilized on the porous substrate for at least about 1week, 1month, or 6months.

17. The method of claim 1, wherein the:
cyclodextrin is selected from the group consisting of α-cyclodextrin, β-cyclodextrin, γ-cyclodextrin, (2,3,6-tri-O-methyl)-β-cyclodextrin, (2,3,6-tri-O-methyl)-β-cyclodextrin, (2-hydroxy)propyl-β-cyclodextrin, (2-hydroxy)propyl-γ-cyclodextrin, random methyl-β-cyclodextrin, random methyl-γ-cyclodextrin, carboxymethyl-β-cyclodextrin, carboxymethyl-γ-cyclodextrin, 6-monodeoxy-6-monoamino-β-cyclodextrin, sulfobutyl-β-cyclodextrin, 6-amino-6-deoxy-β-cyclodextrin, acetyl β-cyclodextrin, succinyl α-cyclodextrin, succinyl β-cyclodextrin, succinyl β-cyclodextrin, (2,3,6-tri-O-benzoyl)-β-cyclodextrin, succinyl-(2-hydroxypropyl)-β-cyclodextrin, and succinyl-(2-hydroxypropyl)-γ-cyclodextrin.

18. The method of claim 14, wherein the porous substrate comprises whatman paper.

* * * * *